(12) United States Patent
Bhakdi

(10) Patent No.: US 12,412,651 B2
(45) Date of Patent: Sep. 9, 2025

(54) SAMPLE TUBE RACK BASED TRANSFER, MANAGEMENT AND TRACKING

(71) Applicant: QuantGene Inc., Santa Monica, CA (US)

(72) Inventor: Johannes Bhakdi, Los Angeles, CA (US)

(73) Assignee: QuantGene Inc., Santa Monica, CA (US)

( * ) Notice: Subject to any disclaimer, the term of this patent is extended or adjusted under 35 U.S.C. 154(b) by 241 days.

(21) Appl. No.: 17/702,571

(22) Filed: Mar. 23, 2022

(65) Prior Publication Data

US 2022/0310238 A1   Sep. 29, 2022

Related U.S. Application Data

(60) Provisional application No. 63/165,072, filed on Mar. 23, 2021.

(51) Int. Cl.
| | |
|---|---|
| G16H 30/20 | (2018.01) |
| G01N 35/00 | (2006.01) |
| G06K 7/14 | (2006.01) |
| G16H 10/65 | (2018.01) |

(52) U.S. Cl.
CPC ....... *G16H 30/20* (2018.01); *G01N 35/00732* (2013.01); *G06K 7/1413* (2013.01); *G06K 7/1417* (2013.01); *G16H 10/65* (2018.01); *G01N 2035/00752* (2013.01)

(58) Field of Classification Search
CPC .... G16H 30/20; G06K 7/1417; G06K 7/1413; B01L 3/5021; B01L 3/50
See application file for complete search history.

(56) References Cited

U.S. PATENT DOCUMENTS

| | | | | |
|---|---|---|---|---|
| 5,993,745 | A * | 11/1999 | Laska | B01L 9/06 211/74 |
| 6,681,363 | B1 * | 1/2004 | Ikeda | H04L 1/0017 714/776 |
| 7,628,064 | B1 * | 12/2009 | Miller | G01F 23/804 422/63 |
| 7,842,246 | B2 * | 11/2010 | Wohlstadter | G01N 21/76 422/52 |
| 7,981,362 | B2 * | 7/2011 | Glezer | B01L 3/50855 422/50 |
| 10,706,247 | B1 * | 7/2020 | Miller | G06K 7/1413 |

(Continued)

*Primary Examiner* — Daniel I Walsh

(74) *Attorney, Agent, or Firm* — Cognition IP, P.C.; Edward Steakley

(57) ABSTRACT

Methods, systems and apparatus for the tracking and managing of biological samples. A provider may check-in or register a patient at a provider facility. A sample tube may be registered to the patient, and a biological sample may be collected. The provider aggregates a plurality of sample tubes into cells of a rack. The provider then captures an image of the rack. A computer vision operation may be performed to isolate and identify a QR code affixed to the lid of each sample tube. The identified sample tubes are registered to the rack in which they are held, and the rack transferred to a destination lab. The same computer vision operation may be performed upon receipt of the rack. The samples may then be transferred to a sample plate. The samples are transferred from a cell in the rack to a corresponding well in the sample plate.

15 Claims, 19 Drawing Sheets

(56) References Cited

U.S. PATENT DOCUMENTS

| | | | | |
|---|---|---|---|---|
| 2002/0069649 | A1* | 6/2002 | Buia | B01L 3/545 62/45.1 |
| 2003/0029916 | A1* | 2/2003 | Merva | G06K 7/10722 235/454 |
| 2004/0033163 | A1* | 2/2004 | Tseung | B65D 1/0223 422/63 |
| 2007/0038406 | A1* | 2/2007 | Uemura | G16Z 99/00 705/2 |
| 2007/0046837 | A1* | 3/2007 | Elberbaum | F16M 13/02 348/739 |
| 2007/0059221 | A1* | 3/2007 | Sorensen | B01L 9/06 422/400 |
| 2008/0063570 | A1* | 3/2008 | Fujino | G01N 35/00732 422/400 |
| 2008/0305515 | A1* | 12/2008 | Burgart | G01N 1/312 435/40.52 |
| 2009/0028754 | A1* | 1/2009 | Robb | B01L 9/06 422/65 |
| 2009/0136386 | A1* | 5/2009 | Duffy | F16K 99/003 422/400 |
| 2009/0220379 | A1* | 9/2009 | Wakamiya | G01N 35/025 422/65 |
| 2009/0324032 | A1* | 12/2009 | Chen | G06T 7/0008 382/128 |
| 2010/0025464 | A1* | 2/2010 | Trueeb | B01L 3/545 235/375 |
| 2010/0028124 | A1* | 2/2010 | Lackner | G01N 35/028 422/63 |
| 2010/0049358 | A1* | 2/2010 | Koch | G06F 17/00 700/214 |
| 2010/0292829 | A1* | 11/2010 | Guzman | B01L 9/06 414/800 |
| 2010/0298108 | A1* | 11/2010 | Sherman | B01L 9/06 494/20 |
| 2012/0009104 | A1* | 1/2012 | Bolotin | B01L 9/06 422/562 |
| 2012/0175328 | A1* | 7/2012 | Bosch | A47B 87/0215 211/85.18 |
| 2013/0019697 | A1* | 1/2013 | McKeen | G01N 35/00029 73/863.21 |
| 2013/0028697 | A1* | 1/2013 | Neeper | G01N 35/04 700/214 |
| 2013/0129166 | A1* | 5/2013 | Muller | B01L 3/502761 382/128 |
| 2013/0132006 | A1* | 5/2013 | Gwynn | B01L 3/021 702/55 |
| 2013/0151004 | A1* | 6/2013 | Winter | G01N 1/42 700/218 |
| 2013/0160533 | A1* | 6/2013 | Fukuma | G01N 35/00584 73/863.01 |
| 2013/0306729 | A1* | 11/2013 | Dilks | G06K 7/10821 235/455 |
| 2013/0333490 | A1* | 12/2013 | Tanoue | G06T 7/74 348/135 |
| 2014/0240100 | A1* | 8/2014 | Johns | B01L 9/06 340/10.6 |
| 2014/0330427 | A1* | 11/2014 | Wilhelm | B65G 1/137 700/217 |
| 2015/0309025 | A1* | 10/2015 | Van Praet | G01N 21/82 435/7.1 |
| 2016/0074865 | A1* | 3/2016 | Rao | B01L 3/5453 138/104 |
| 2016/0327583 | A1* | 11/2016 | Pollack | B01L 9/06 |
| 2017/0192002 | A1* | 7/2017 | Van Praet | G06T 7/60 |
| 2018/0100868 | A1* | 4/2018 | Grimwood | B01L 9/06 |
| 2018/0136096 | A1* | 5/2018 | Foggi | G01N 1/312 |
| 2019/0113533 | A1* | 4/2019 | Waldburger | G01N 35/0092 |
| 2019/0291101 | A1* | 9/2019 | Ambartsoumian | B01L 3/5085 |
| 2019/0378292 | A1* | 12/2019 | Rempel | G06T 7/70 |
| 2020/0072857 | A1* | 3/2020 | Oda | G01N 35/026 |
| 2020/0191812 | A1* | 6/2020 | Dilks | G06K 7/10861 |
| 2020/0341019 | A1* | 10/2020 | Cinti | G07F 11/62 |
| 2021/0311082 | A1* | 10/2021 | Tesluk | G01N 35/1011 |
| 2022/0307069 | A1* | 9/2022 | Bhakdi | C12Q 1/686 |
| 2022/0310238 | A1* | 9/2022 | Bhakdi | G06K 7/1413 |
| 2023/0114049 | A1* | 4/2023 | Newman-Lehman | C12Q 1/6844 435/287.2 |
| 2023/0204617 | A1* | 6/2023 | Stumpf | G01N 35/0099 73/863.01 |
| 2023/0408536 | A1* | 12/2023 | Ostergaard | G01N 35/0092 |

\* cited by examiner

```
┌─────────────────────────────────────────────────────────────┐
│ Capture one or more images of a rack, wherein the rack holds │──── 1501
│ one or more test tubes and wherein each test tube holds a    │
│ biological sample                                            │
└─────────────────────────────────────────────────────────────┘
                              │
┌─────────────────────────────────────────────────────────────┐
│ analyze the one or more images to determine orientation of   │──── 1502
│ the rack, identify each test tube, read the QR code on each  │
│ test tube and associate each test tube with a patient based  │
│ on the read QR code                                          │
└─────────────────────────────────────────────────────────────┘
                              │
┌─────────────────────────────────────────────────────────────┐
│ Store information related to the rack, each test tube held   │──── 1503
│ by the rack and the patient associated with each test tube   │
└─────────────────────────────────────────────────────────────┘
                              │
┌─────────────────────────────────────────────────────────────┐
│ Transfer the rack from a provider location to a destination  │──── 1504
│ lab                                                          │
└─────────────────────────────────────────────────────────────┘
                              │
┌─────────────────────────────────────────────────────────────┐
│ Receive the rack at the destination lab                      │──── 1505
└─────────────────────────────────────────────────────────────┘
                              │
┌─────────────────────────────────────────────────────────────┐
│ Capture one or more images of a rack and analyze the images  │──── 1506
└─────────────────────────────────────────────────────────────┘
                              │
┌─────────────────────────────────────────────────────────────┐
│ Identify each test tube, read the QR code on each test tube  │──── 1507
│ and retrieve patient information based on the QR code        │
└─────────────────────────────────────────────────────────────┘
                              │
┌─────────────────────────────────────────────────────────────┐
│ Associate the rack with a sample plate and transfer the      │──── 1508
│ biological samples from the test tubes in the rack to        │
│ corresponding plate wells in the sample plate                │
└─────────────────────────────────────────────────────────────┘
                              │
┌─────────────────────────────────────────────────────────────┐
│ Perform a PCR test procedure for each biological sample on   │──── 1509
│ the sample plate                                             │
└─────────────────────────────────────────────────────────────┘
                              │
┌─────────────────────────────────────────────────────────────┐
│ Analyze the results of the PCR test procedure                │──── 1510
└─────────────────────────────────────────────────────────────┘
```

FIG. 15

SAMPLE TUBE RACK BASED TRANSFER, MANAGEMENT AND TRACKING

CROSS-REFERENCE TO RELATED APPLICATIONS

This application claims the benefit of U.S. application Ser. No. 63/165,072 filed on Mar. 23, 2021, which is incorporated herein by reference in its entirety.

FIELD

The present invention relates generally to the managing and tracking of biological samples, the use of computer vision to recognize the containers that hold the samples to visually register and verify the possession of the samples and the analysis of biological samples through the use of machine learning models.

BACKGROUND

In a traditional approach to collection and testing of biological samples from patients at a provider facility, a nurse or technician would collect a sample from the patient and mail or transfer that sample to a laboratory for processing. At the laboratory, the samples are received and must be entered into the laboratory system. The labels may have different labeling on them when they come from different providers. The lack of organizing of the received samples leads to a slow process that is prone to error. For example, a laboratories that processes 15,000 biological samples a day will need to employ 150 full time employees to perform sample accessioning.

The process of receiving the samples, entering the samples into the system and accessioning/transferring the samples is not even fully digital. In most cases a lab technician would need to scan all of the received tubes holding the samples to enter them into the system. In some cases the lab technician would enter the received samples into the system manually through a keyboard or other input method. The lab technician would then create a list of the sample tubes received and print the list. At this point the lab technician or sample accessioning technician would take the sheet and use it to document the transference of samples from the tubes to wells in a sample plate. The technician would mark the well number next to the tube entry on the printed list/sheet. The technician may also need to write labels on the tube to indicate the position of the sample in the sample plate, next to the tube well number in which then writes, next to each tube, the well number.

After the technician has transferred all the samples into the sample plate and documented the locations of the samples, the technician then needs to enter that information into the system. This entry is usually performed manually and may be prone to errors. The errors may arise from the initial entry of the samples into the system upon reception, transference of samples from unorganized sample tubes, the documenting of the well number for the samples, the entering of the documented well numbers for the samples or a number of other human errors.

SUMMARY

The systems and methods described herein provide for the tracking and managing of biological samples. In one embodiment, a one or more providers may collect a biological samples from one or more patients at a provider facility. The provider may use a provider device, connected to a provider terminal, either wired or wirelessly. A dashboard, terminal or portal may be displayed to the provider through a display connected to the provider terminal or the provider device.

The provider device and provider terminal may be in communication with one or more databases, one or more application servers and one or more analysis servers. In some embodiments, the provider may collect a biological samples from a patient. The collected biological sample may then be placed into a sample container, such as test tube or vial. The test tube may have one or more labels or visual indicators affixed. For example, a QR code may be affixed to the top or lid of the test tube and a barcode may be affixed to the side of the test tube.

The labeled test tubes may be aggregated into one or more racks, wherein the one or more racks are arranged in a grid pattern with coordinates for the rows and columns. The rack may also have a have a QR code, visual marker, fiducial marker, landmark or other physical or visual indicator of the orientation of the rack.

In some embodiments, a provider may capture one or more images with a provider device. Provider devices may include smartphones, tablets, laptops or other devices with one or more camera sensors configured to capture images of the rack. The one or more images of each rack may be analyzed to identify the orientation of the rack within the captured images, identify one or more test tubes held by the rack, read a QR code for each identified test tube and associate each test tube with a patient based on the read QR code. The association and registration of the patient with their sample, the sample with the test tube and the test tube with the rack may be tracked and monitored by the system and stored in the provider terminal, an application server, an analysis server and/or a database. Information related to the one or more racks, the test tubes held by each rack and the patients associated with each test tube may also be stored.

In some embodiments, a status of each rack and each sample may be maintained in a central location, and accessible by the patient, the provider or the lab. The status of the racks and test tubes may be updated in real-time at each step in the process. Every action and interaction with a rack or sample may generate an update to the status and the information associated with the rack or sample.

The dashboard, terminal or portal may display information related to the rack and samples in real-time as they are updated. Push notifications may be generated to alert providers, lab workers and patients of any changes in the processing of their sample, including location of their sample, progress of their sample in the testing process and results of the testing performed on the sample.

In some embodiments, the provider facility may initiate a transfer of the racks to a destination lab for processing. Upon receipt of the racks, a lab device may be used to capture images of each rack. The images may then be analyzed to identify the racks, read QR codes from the test tubes, retrieve patient information associated with each test tube and verify/validate the received racks/sample. The analysis may be used to guarantee that all samples are accounted for, maintaining a clear chain of custody and an auditable trail.

In some embodiments, after analyzing and validating the received racks and samples, each rack may then be associated with a corresponding sample plate. Each biological sample from a rack may then be transferred to the sample plate associated with it. The biological samples may be transferred from each test tube to a plate well of the sample plate. The plate well position of transferred biological sample directly corresponds to the rack position of the test tube that the sample was transferred from.

The sample plate may be transferred or loaded into a PCR system. A PCR test procedure may then be initiated for each sample plate of the sample plate. Upon performing the PCR testing procedure on each biological sample, an analysis may be performed on the results of the PCR test procedure. The analysis may be performed by one or more machine learning models operating on an analysis server, lab device, application server, lab terminal or any system with memory for storing the machine learning model, information related to the PCR test for each sample and a processing unit to execute the one or more machine learning models.

In some embodiments, the one or more machine learning models may assign a confidence level to each result. Results with a confidence level at or above a predetermined threshold level may be considered accurate. Each accurate result may be associated/linked/added to a patients record and stored in the database, application server and/or analysis server to. The results may also be stored without the association with a patient in an anonymized manner to protect the identity of the patient. A hash or distributed ledger may be used to store personal information of the patient and the results of the testing. Distributed ledgers such as block chain may be used in the implementation. Public-private key encryption may also be used in the authorization verification when accessing stored patient records, provider records or lab records.

In some embodiments, the patient records may be hashed. At each update, the updated information may be added to the hashed record and hashed again. This may be used to maintain a secure audit trail that cannot be modified. Both public and private keys may be used in the hashing.

In some embodiments, a qualified user may be alerted for each result with a confidence level below a predetermined threshold. Qualified users may be users qualified to analyze PCR test results, such as a lab director, lab specialist or a user with sufficient training to allow them to perform the analysis. Upon receiving the alert, the qualified user may perform an analysis on the PCR test results. The determination made by the qualified user may then be stored as is disclosed above.

BRIEF DESCRIPTION OF THE DRAWINGS

The present disclosure will become better understood from the detailed description and the drawings, wherein:

FIG. 12 is a diagram illustrating an exemplary rack management interface in accordance with aspects of the present disclosure.

FIG. 15 is a flow chart illustrating an exemplary method that may be performed in accordance with some embodiments.

DETAILED DESCRIPTION

Figure 1:
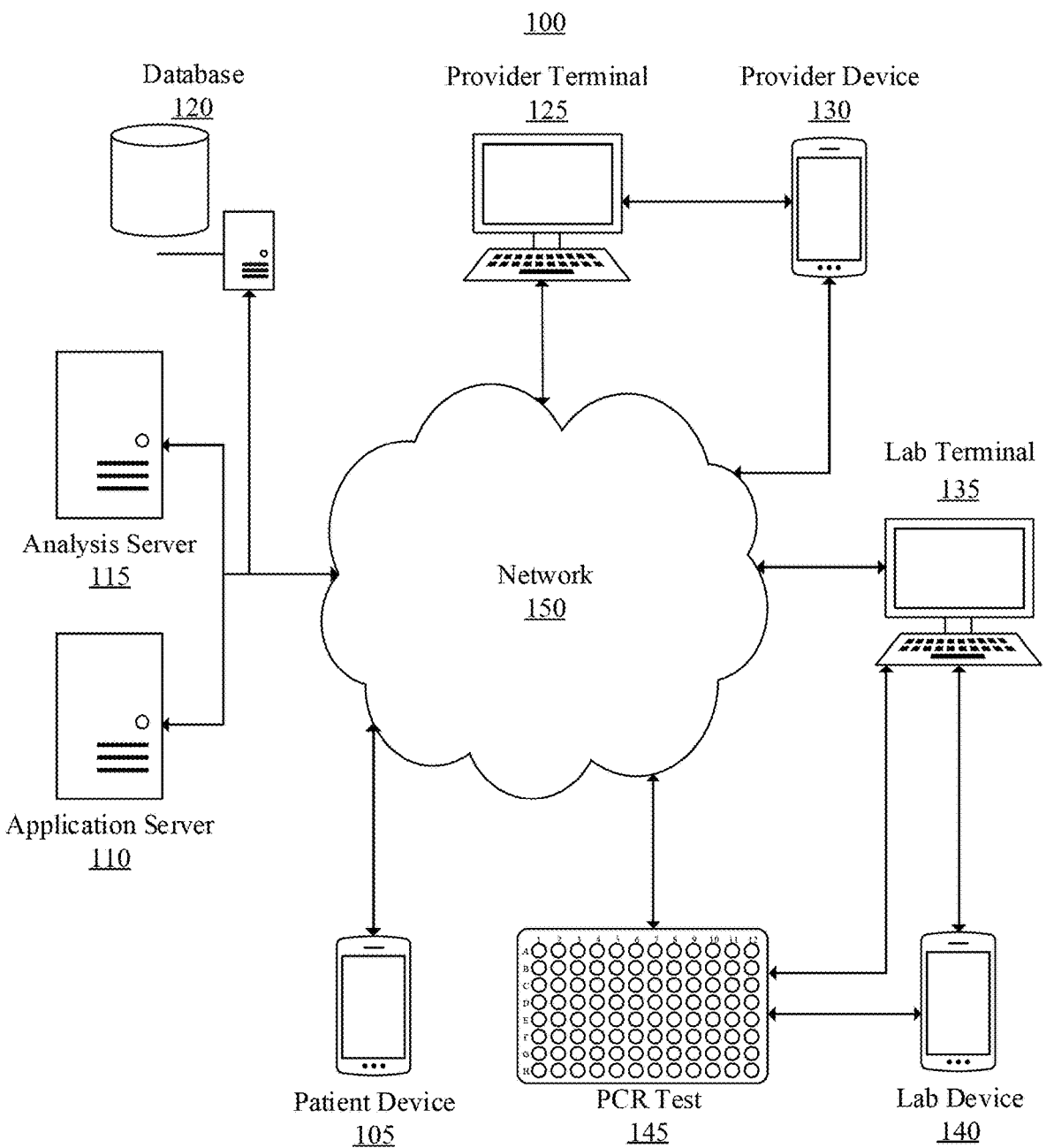
FIG. 1 is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

The following generally relates to a system and methods for managing and tracking both small and large numbers of biological samples from a provider facility to a testing facility (destination lab). The disclosed system and methods may provide accelerated testing speed and accuracy during times of high testing demand, such as during a pandemic (SARS-CoV-2) and for other industries such as food manufacturing. In some embodiments, a database, application server, analysis server, lab terminal and provider terminal may be configured to operate cooperatively as a cloud based system. All patient data may be stored on the cloud, either in the database, application server, analysis server, lab terminal or provider terminal.

In some embodiments, a patient may enter a provider facility to have a biological sample taken and tested. A provider/nurse may receive the patient and check the patient into the system. If the patient is not already registered into the system, the nurse may then create a new patient record for the patient. The checking in of the patient and registering of a new patient may be performed on a provider terminal or a provider device, such as a tablet computer or smartphone. After the check-in or registration of a new user, the nurse may select the patient in the system and scan a barcode or QR code on a test tube to associate the test tube to the patient. At this point, the same or different nurse may use the test tube to collect a biological sample from the patient. The registration and collection may be performed in the same location, such as in a room designated for the collection of biological samples or in a drive-through setting, where the registration, scanning and sample collection may be performed on a patient while they remain in their vehicle (i.e. SARS-CoV-2 drive-through/drive-up testing). Alternatively, the patient may be given the tube and instructed to proceed to another location with the tube to have the biological sample collected.

In some embodiments, upon collection of a biological sample from a patient, the nurse may place the tube containing the sample into a rack. The aggregation of the samples into one or more racks provides a central organized storage for all collected samples, reducing the possibility of losing samples and errors.

The rack allows for the storage and transportation of sample tubes. Sample tubes may be loaded in any order or rearranged. Sample tubes may be replaced/exchanged with sample tubes from other racks. Additional sample tubes may be added to racks that are not full. The changing, exchanging, adding, replacing and removing of sample tubes may all be performed without losing any of the information associated with the sample tubes.

For example, there may be many racks that are only partially filled. The sample tubes may be aggregated so as to use the least number of racks possible. The sample tubes may be moved from one or more partially full racks to another partially full rack until all racks are full or all but one is full, with the partially full rack being organized with sample tubes occupying positions starting from the top left of the rack (increases downward and to the right).

Images of the racks may be captured and analyzed to identify the tubes held in the rack. Racks may be full or partially full. The identified tubes may be associated with the rack and tracked throughout the testing process. If any changed are made to the rack, such as tubes being removed, added or exchanged, the racks that have been affected would need to be imaged and analyzed again, and the record for the rack and tube would need to be updated on the system. This is much faster and efficient and less error prone that the traditional method of adding or removing samples from a batch of samples to be analyzed. Traditionally, a provider would need to find the tube in a batch of tubes, remove the tube, find the record of the tube in the system and remove it from the batch. In an unorganized collection of tubes, it may be hard to find the tube that is to be removed. When a tube needs to be removed from the disclosed invention, the provider may be given the rack location and the position of the tube within the rack. This allows for the provider to instantly know where the tube is. In this example, when a tube is removed from a position that is not the last occupied position of the rack, the tube in the last position of the rack or a new tube may be placed in the empty, previously occupied position.

At the provider location, a nurse or other provider employee may capture images of the racks, package the racks in compliance with a transportation method to be used to transfer the racks to a destination facility and initiate the transfer (i.e. mail, courier, walking, intern) of the racks to the destination facility.

At the destination lab, a lab tech may receive the one or more racks from one or more provider facilities as well as individual samples mailed from patients. The destination lab may receive samples in a mixed format (i.e. some bagged and some in racks). Upon receipt, the lab tech may capture images of the one or more racks, in a similar manner to that described above. The analysis of the images may be used to verify that all the samples were received as well as retrieve patient information and update the status of the racks and samples.

In some embodiments, the racks may be processed (i.e. image analysis/scanning and sample transfer) as they are, even if the racks are only partially full. In some embodiment, the racks may be scanned as they are, even if the racks are only partially full, for verification purposes, but additional tubes may be added to fill up the empty spaces before sample transfer to a sample plate. In this embodiment, after verification of the partially full rack additional sample tubes may be placed into empty slots of the rack and scanned into the system to register the additional sample tubes with the current rack/batch of samples being tested. This would minimize the number of racks needed to hold the sample tubes, the number of sample plates to transfer the samples to and the number of testing runs (PCR).

In some embodiments, racks that are partially full may have additional sample tubes placed in the open spaces in order to fill as much of the rack as possible. The additional sample tubes may be samples received in the mail directly from patients, from bagged sample tubes, sample tubes of samples that need to be rerun or sample tubes from other racks. After filling a rack with additional sample tubes, the rack may then be processed. Scanning of the full rack with a mix of original sample tubes and new sample tubes may be used for verification of sample receipt. Upon scanning, the samples tubes may be checked against a manifest to guarantee that all samples are accounted for. This manifest may be stored on the database and verified and updated at each step of the process. This manifest may use a distributed ledger to maintain an uncompromisable audit trail and log of all activities related to each sample batch, each rack and each sample. The manifest may be hashed at one or more levels.

In some embodiments, after receiving, scanning and updating the status of the racks and samples, a sample accessioning tech or lab tech may transfer the samples from the rack to a sample plate. The tech may need to open each sample tube, collect a portion of the sample held and transfer collected portion of the sample to a well in the sample plate. The transferring may be performed in same order as the tubes are positioned in the rack. For example, a rack that holds 94 sample tubes may be labelled with columns 1-12 and rows A-H. The labelling may be displayed on the rack itself or may be implicit and only used in the recordation of the position of sample tubes. The rack will not have open cells in the positions of A1 and A2, as these are reserved for control positive and control negative. The asymmetry of having a solid blank space on the upper left corner may be used to orient the rack during a computer vision analysis of the rack. The tech may collect and transfer a portion of the sample from sample tube at position C1 on the rack to well C1 on the sample plate. This process follows with collecting and transferring samples from D1-D1, E1-E1, F1-F1, G1-G1, H1-H1, A2-A2 . . . H12-H12. Well A1 may contain a control positive sample and well B1 may contain a control negative sample.

In some embodiments, each sample plate may be fed into the PCR machine for processing. Upon completion of the PCR run, the PCR curves produced for each sample may then be transferred to a database for storage and an analysis server to be analyzed. The status of the rack and samples held by the rack may be updated to show that the processing of the sample has been completed and that the results are being analyzed.

FIG. 1 shows a diagram illustrating an exemplary environment of a sample collection and management system 100 in accordance with aspects of the present disclosure. The system 100 may comprise patient device 105, application server 110, analysis server 115, database 120, provider terminal 125, provider device 130, lab terminal 135, lab device 140, PCR system 145 and network 150.

Patient device 105 may be an example of, or include aspects of, the corresponding element or elements described with reference to FIG. 2. Patient device 105 may be one or more personal computers, personal digital assistants (PDAs), tablet computing devices, laptop computers, smart phones, e-readers or other systems capable of operating a standalone application or web-based application in a browser. Patient device 105 may be in communication with one or more application servers 110 and one or more databases 120 through network 150.

Application server 110 may be an example of, or include aspects of, the corresponding element or elements described with reference to FIG. 3. Analysis server 115 may be an example of, or include aspects of, the corresponding element or elements described with reference to FIG. 4. Application server 110 and Analysis server 115 may be different machines, the same machine, virtual machines on different machines, virtual machines on the same machine, different machines at different locations or combination thereof, and connected to one another through network 150. Application server 110 and Analysis server 115 may be in communication with patient device 105, database 120, provider terminal 125 and lab terminal 135 through network 150.

Provider terminal 125 may be an example of, or include aspects of, the corresponding element or elements described with reference to FIG. 5. Provider device 130 may be an example of, or include aspects of, the corresponding element or elements described with reference to FIG. 6. Lab terminal 135 may be an example of, or include aspects of, the corresponding element or elements described with reference to FIG. 7. Lab device 140 may be an example of, or include aspects of, the corresponding element or elements described with reference to FIG. 8.

PCR System 145 may be any PCR machine or sets of machines configured to system to amplify segments of DNA via the polymerase chain reaction (PCR). PCR system 145 may be any thermocycler, real-time PCR system, DNA amplification system, protein-misfolding cyclic amplification (PMCA) system, or other system configured to facilitate other temperature-sensitive reactions for rapid diagnostics. PMCA systems may be used for the detection of prions in the biological samples being tested. This may be used in the testing cattle for bovine spongiform encephalopathy (mad cow disease) and testing cattle feed for prions which may cause bovine spongiform encephalopathy. Similarly, this system may be used for the high throughput of testing for chronic wasting disease (CWD) in wild population of deer, elk, reindeer, sika deer and moose. Other industries that require large number of tests to be performed may also benefit from the disclosed system and methods, such as food manufacturing. Batch tests may be performed on samples from food manufacturing facilities to identify pathogens such as, Norovirus, *Salmonella, Clostridium perfringens, Campylobacter, Staphylococcus aureus* (Staph), *Clostridium botulinum* (botulism), *Listeria, Escherichia coli* (*E. coli*), *Vibrio,* Cyclospora, Hepatitis A and other foodborne pathogens.

Figure 2:
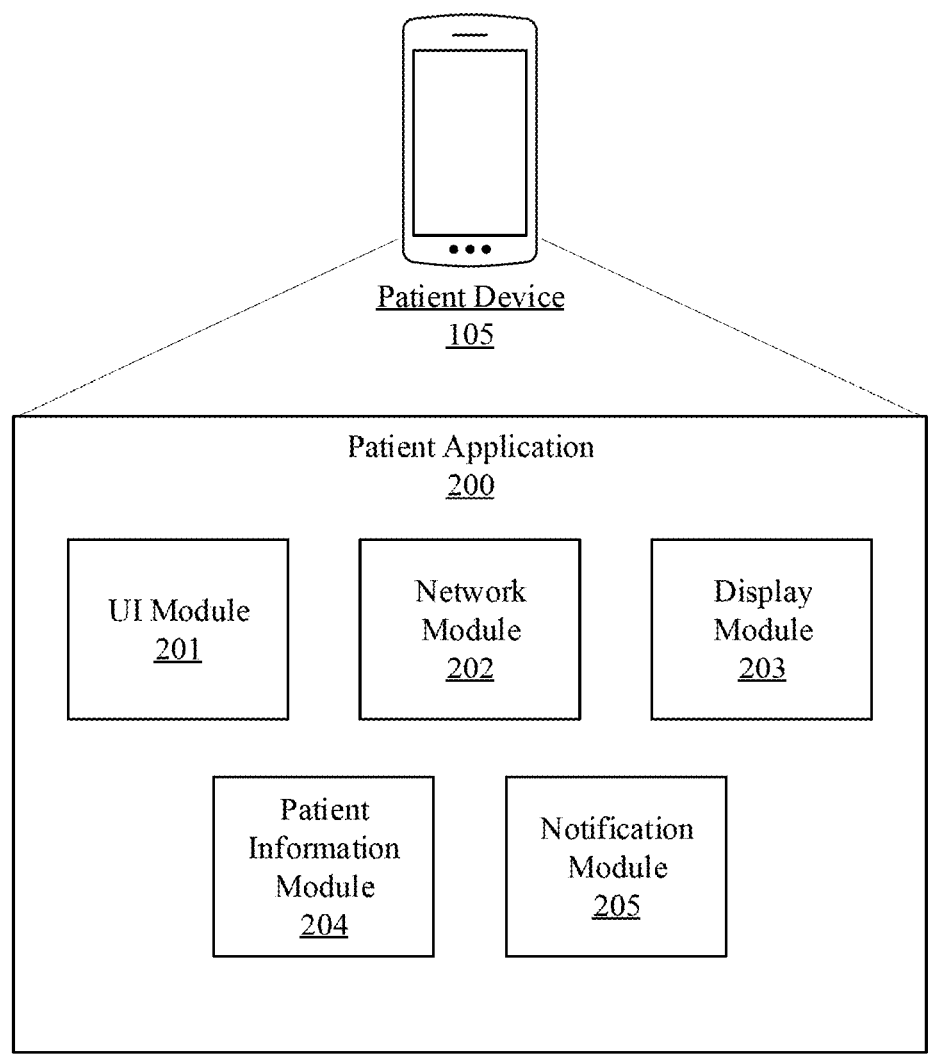
FIG. 2 is a diagram illustrating an exemplary patient device in accordance with aspects of the present disclosure.

FIG. 2 is a diagram illustrating an exemplary patient device 105 in accordance with aspects of the present disclosure. Patient device 105 may comprise patient application 200, UI module 201, network module 202, display module 203, patient information module 204 and notification module 205.

UI module 201 may generate a user interface to allow the user to manage their medical records, appointments, prescriptions, test results and/or other information and processes relating to a healthcare provider or diagnostic facility. The UI module 201 may also allow the user to edit or modify information maintained on the application server and database. Information pertaining to samples collected from a patient may be displayed to a user in a manner to facilitate tracking of the sample from the collection until the completion of the diagnostics performed on the sample and the result of such diagnostics or testing. The UI module 201 may receive information associated with a patient sample from the patient information module 204 or the notification module 205. Notification updates received from the notification module 205 may have a graphical representation created by the UI module 201 and displayed by the display module 203.

Network module 202 may transmit and receive network signals and receive signals from other computing systems via a network. In some examples, the network module 202 may enable transmitting and receiving signals from the Internet. Signals received by the network module 202 may be used by the other modules. The modules may transmit signals through the network module 202.

Display module 203 may be a touch-screen display, a head-up display, a head-mounted display, an optical see-through display, an optical see-around display, a video see-through display, a flat-panel display, a light-emitting diode (LED) display, an electroluminescent display (ELD), an electrophoretic display (EPD or electronic paper), a liquid crystal display (LCD), an organic LED (OLED) display, an active-matrix organic light-emitting diode display or any other type of display on a display device.

Patient information module 204 may access application server 110 and database 120, retrieve patient records and information, and store those records and information locally on the patient device. The patient information module 204 may also store, update and transfer patient records and information entered by the patient through the UI module 201.

Notification module 205 may receive push notifications or other forms of alerts/notifications from the application server 110, analysis server 115, provider terminal 125 or lab terminal 135. The notification module 205 may also periodically check records associated with the patient for any updates, and notify the patient of any changes that have been made. The notification module 205 may also be configured to monitor the status of a sample being sent out for testing at a lab. The notification module 205 may periodically alert the user of the progress of the sample and provide any analysis and results associated with the sample.

Figure 3:
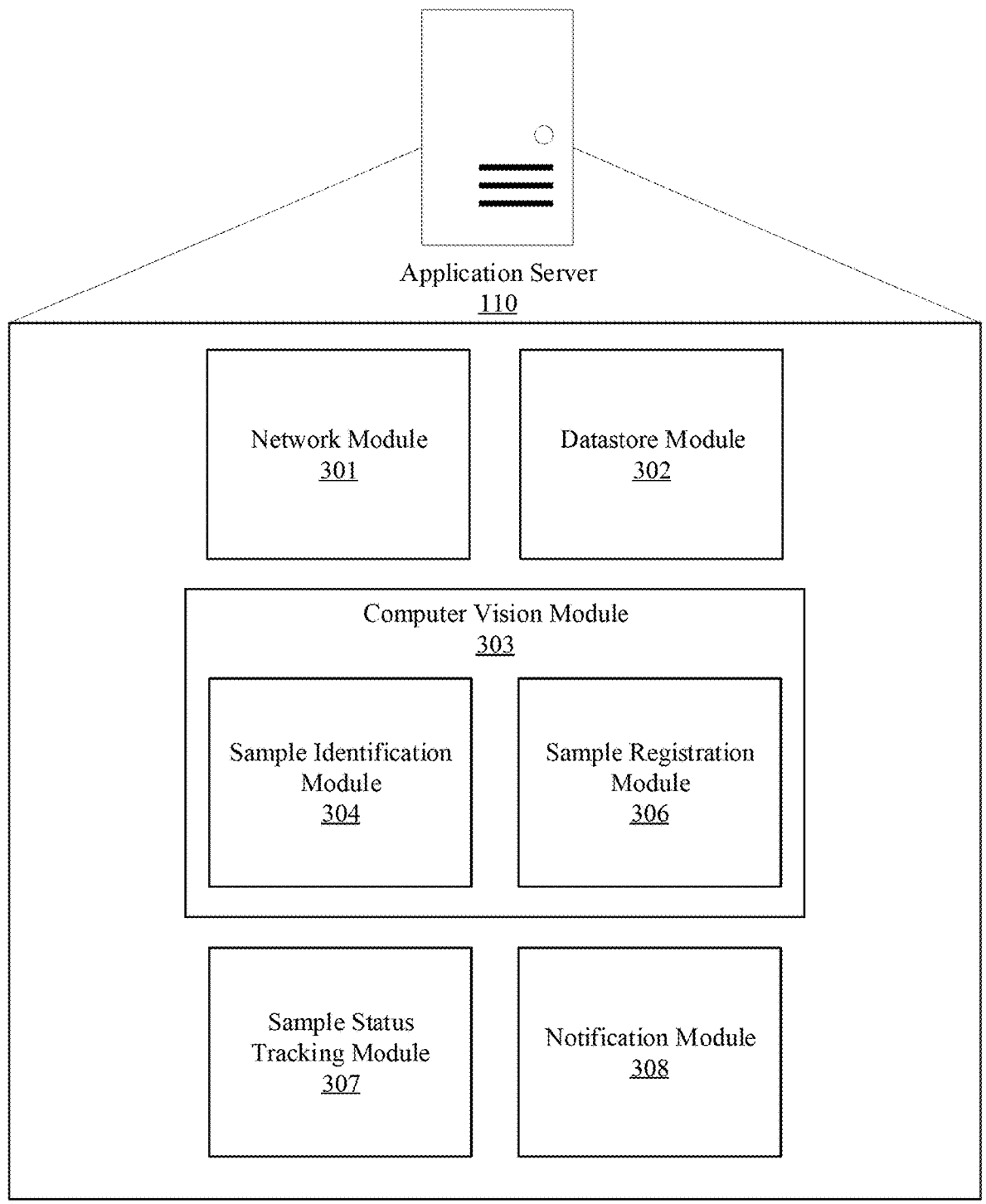
FIG. 3 is a diagram illustrating an exemplary application server in accordance with aspects of the present disclosure.

FIG. 3 is a diagram illustrating an exemplary application server 110 in accordance with aspects of the present disclosure. Application server 110 may comprise a network module 301, datastore module 302, computer vision module 303, sample status tracking module 307 and a notification module 308.

Network module 301 is similar in function to that of network module 202, and therefore not described in detail for sake of brevity.

Datastore module 302 may receive and serve information associated with patients, biological samples, batches of samples, racks holding sample tubes and other information necessary to manage, track, monitor otherwise process collected biological samples. The provider terminal 125 may provide information to the datastore module 302 relating to a batch of samples collected at the provider facility and being transferred to a destination facility for processing. Each sample record created at the provider facility, including status/progress, location, patient ID, rack ID, batch ID, collection time, destination facility, test to be performed, sample tube barcode, sample tube QR code and/or other information related to the collected sample, may be received and stored by the datastore module 302. This information may be provided to the sample status tracking module 307 to facilitate the logging and tracking of each sample. The registration of each patient with a sample tube, the barcode/QR code on the sample tube, the biological sample, the results of the diagnostics performed on the sample and the progress/status of the sample throughout the process may be handled by the application server 110 and stored locally by the datastore module 302. A local copy of the data associated with the biological samples currently registered in the system may be stored from the initial registration of the patient with a sample tube before collection, until the results have been provided to the patient and stored locally on the patient device 105.

Computer vision module 303 may comprise a sample identification module 304, visual tracking module 305 and sample registration module 306. The computer vision module 303 may be implemented on the application server 110, provider terminal 125, provider device 130, lab terminal 135, lab device 140 or combination thereof. The computer vision module 303 may receive one or more images of one or more racks. The images may be captured at the provider facility or at the destination facility. At the capturing device, a provider/nurse/lab tech may capture one or more images or video of one or more racks. The provider may select and drag a bounding box a displayed image to provide an orientation and region of interest to be analyzed. A rectangular region may also be displayed on the device in which the provider must align the rack with the box before an image may be captured. These images and/or videos are then processed by the computer vision module 303.

Sample identification module 304 may analyze the one or more images of each rack to identify the orientation of the rack within the captured images if the orientation has not already been specified by the provider or lab technician. The sample identification module 304 may further identify one or more test tubes held by the rack, drawing a bounding sub-box around each sample and extracting and analyzing each of the regions of interest contained within each sub-box to further identify a QR code affixed to the top surface or portion (e.g., lid) of a sample tube/test tube. The identified QR codes may then be read for each identified test tube and the test tube may then be associated/registered, by the sample registration module 306, with a patient based on the read QR code. The association and registration of the patient with their sample, the sample with the test tube and the test tube with the rack may then be tracked and monitored by the sample status tracking module 307 and/or otherwise stored in the provider terminal 125, provider device 130, lab terminal 135 and/or lab device 140.

If the sample identification module 304 is unable to identify a sample tube and the affixed QR code from the one or more images, the provider or lab technician may be prompted to recapture an image of the entire rack to attempt the analysis, identification and registration again.

In some embodiments, the provider or lab tech may capture one or more images of the rack and sample tubes held by the rack from a closer position. The images may also be captured at a higher magnification level or zoomed-in on. The image may not include the entire rack, but only the sample tubes unable to be identified and those in close proximity to it. The identification of the position of the sample tube of interest may be determined based on the identification of the previously identified sample tubes proximate to the unidentifiable sample tube. The system may then analyze the portion of the image in the identified position to recognize the QR code of the previously unidentifiable sample tube. The system may analyze an image and determine objects representing the respective test tubes in a rack. The system may correlate the respective objects to an x/y position of the rack. For example, the rack may have a x/y numbering scheme of letter (e.g., A, B, C, etc.) to represent rows, and numbers (e.g., 1, 2, 3, etc.) to represent columns. The system may process the image and identify respective test tube object in spatial relationship to a fiducial marker in an upper left portion of a sample rack to determine the respective position of an individual test tube, and its corresponding x/y coordinate within the rack.

In some embodiments, the provider or lab tech may remove the unidentifiable sample tube and capture an image of the QR code on top of the unidentifiable sample tube or the barcode on the side of the unidentifiable sample tube. A provider or lab tech may also use a handheld or stationary barcode/QR code scanner to register the unidentifiable sample tube.

After removing the unidentifiable sample tube, the lab technician may also manually enter an ID number or other information from the barcode or other labels on the unidentifiable sample tube.

Sample status tracking module 307 may receive status updates from provider terminals and/or provider devices upon scanning of the sample tubes and registering of the tubes in the one or more racks. The provider terminal may also send updates on the status of racks, batches of racks, and individual samples held in sample tubes held by the racks when not only capturing images of the racks for registration, but also upon initiating a transfer of the batch of racks from the provider facility to the destination facility and upon the physical handoff from the provider to a courier service to carry out the transfer. The sample status tracking module 307 may also access external servers, databases, applications, websites and/or APIs to receive updated information from the courier service or other third parties that may handle the racks between the provider facility and the destination facility. Upon arrival of the racks at the destination facility, the scanning and imaging of the racks and the sample tubes held in each rack may trigger an update to be sent directly to the sample status tracking module 307. This may happen if the sample identification and registration is performed at the lab terminal 135. If the captured images are sent to the application server for identification and registration, the sample status tracking module may instead receive the status update information from the computer vision module 303 or the datastore module 302.

In some embodiments, the analysis server 115 may provide status information to the sample status tracking module 307. The updates from the analysis server 115 may include the analysis and results of the diagnostic tests (positive, negative or invalid) as well as the progress (completed, processing, sample being rerun).

Notification Module 308 may relay updates received by the sample status tracking module 307 to patient devices, lab terminals, and provider terminals. The notification may be displayed to the lab techs, providers and patients, providing a direct link to the associated information in a dashboard or portal interface.

Figure 4:
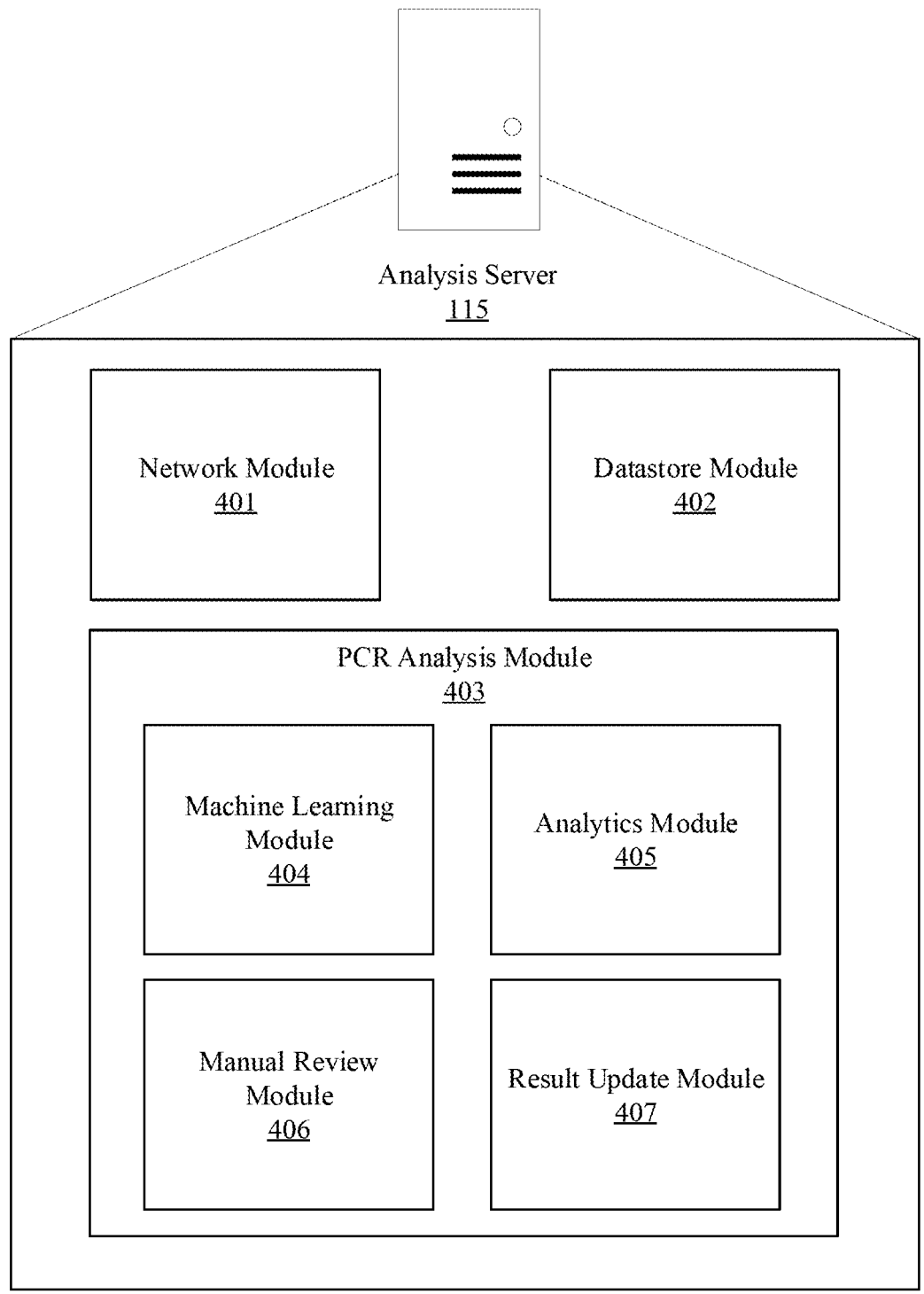
FIG. 4 is a diagram illustrating an exemplary analysis server in accordance with aspects of the present disclosure.

FIG. 4 is a diagram illustrating an exemplary analysis server 115 in accordance with aspects of the present disclosure. Analysis server 115 may comprise network module 401, datastore module 402 and PCR analysis module 403. Network module 401 and datastore module 402 are similar to the network module 301 and datastore module 302 of FIG. 3 and will not be described in detail for the sake of brevity.

PCR analysis module 403 may comprise a machine learning module 404, analytics module 405, manual review module 406 and result update module 407. The PCR analysis module 403 may be responsible for the automated analysis of results received from PCR test 145 systems at one or more destination labs. A large number of labs and PCR systems may use a single analysis server. Clusters of analysis servers may also be used to process the PCR curves received from a plurality of labs.

The PCR analysis module 403 provide the received PCR curve data to the machine learning module 404. The machine learning module 404 may use one or more machine learning modules to analyze the received PCR curves and to classify the results of the curves. The machine learning module 404 may also be configured to calculate a confidence level for each PCR curve classified. Results with a confidence level at or above a predetermined threshold level may be considered accurate. Each accurate result may be associated/linked/added to a patients record and updated on in the database and the application server 110 by the result update module 407. The analytics module 405 may also receive the results of the analysis, with or without attached patient information. When stored without the associated patient information, the analysis data may be used in an anonymized manner to protect the identity of the patient.

Manual review module 406 may be configured to alert a qualified user of an invalid analysis result or a result with a confidence level below the predetermined threshold. A qualified user may be the lab director or a lab tech trained on interpreting and analyzing PCR curves. Upon receiving the alert, the manual review module 406 may provide an interface to the qualified user for selecting a classification for each displayed result. The PCR curves may be displayed in a graphical user interface, with the PCR curve graph of each invalid or low confidence result disposed over the well position of the sample. In some embodiments, the invalid and low confidence results may be queued for analysis by the qualified user. The queued results may be grouped by similarity and displayed to the qualified user at the same time. The qualified user may be given the option to make a single classification selection to classification all of the results, make a classification selection for each result or select multiple results to include in a group classification selection to classify all the result of the selected results.

Figure 5:
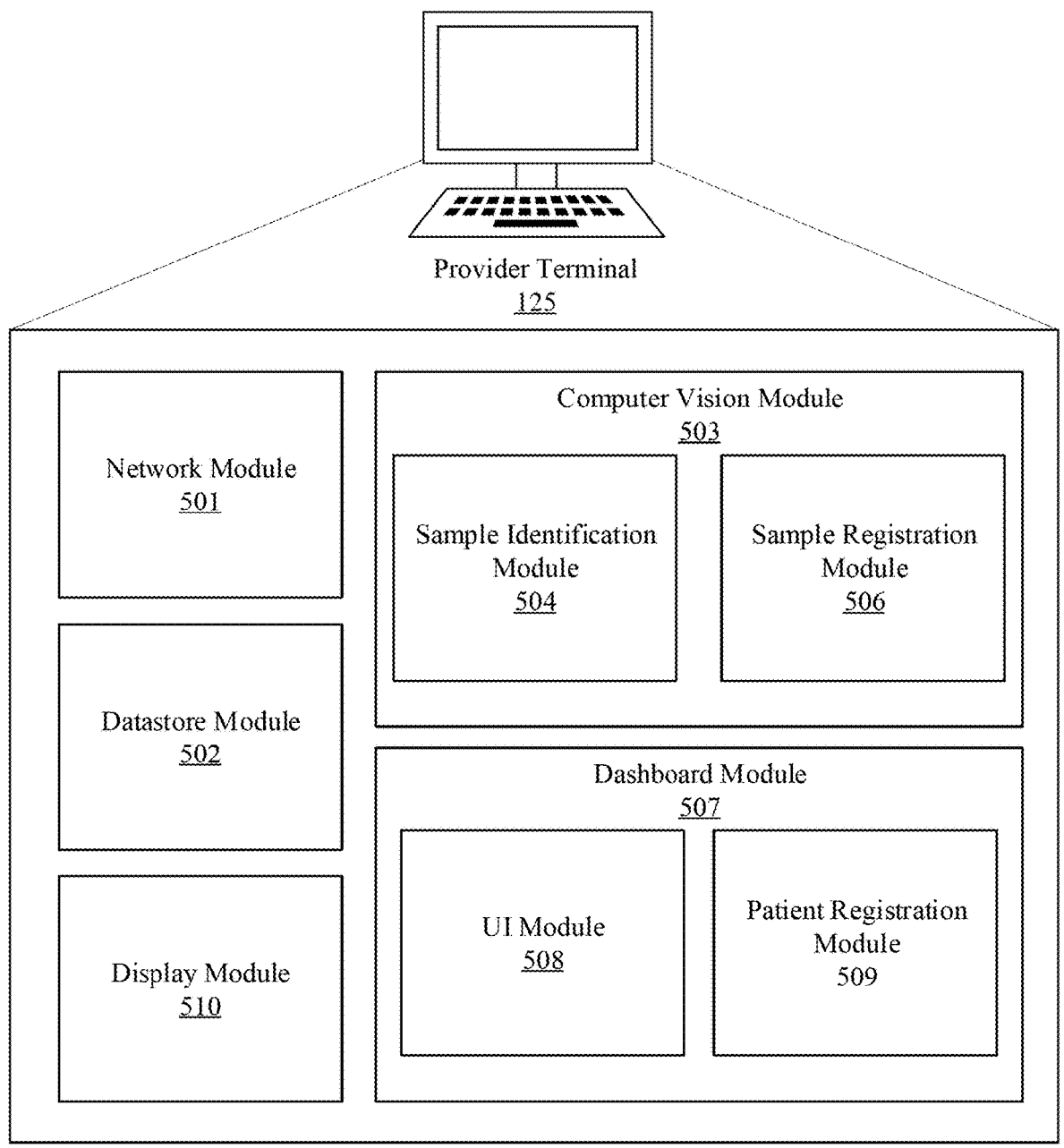
FIG. 5 is a diagram illustrating an exemplary provider terminal in accordance with aspects of the present disclosure.

FIG. 5 is a diagram illustrating an exemplary provider terminal 125 in accordance with aspects of the present disclosure. Provider terminal 125 may comprise a network module 501, datastore module 502, computer vision module 503, dashboard module 507 and a display module 510.

The network module 501, datastore module 502, computer vision module 503, sample identification module 504, sample registration module 506 and display module 510 may be similar in function to that of network module 301, datastore module 302, computer vision module 303, sample identification module 304, sample registration module 306 and display module 203 and therefore not described in detail for sake of brevity.

Dashboard module 507 may comprise UI module 508 and patient registration module 509. The dashboard module 507 may manage display of UI components generated by UI module 508. A dashboard, terminal or portal may display information relating to patients, collected samples, racks holding the samples and batches of racks. The displayed UI components generated by the UI module 508 may allow a provider to check-in a patient or create a new patient. After checking the patient in, the dashboard may display patient information for the one or more patients currently checked-in. Sample tube IDs may be associated with each patient from which a biological sample has been or will be collected. The dashboard may also display information related to each sample in a batch of samples as well as a visual representation of the position of samples in the one or more racks. The UI module may update the rack and samples information in real-time.

Patient registration module 509 may receive patient information entered by the provider in the dashboard. Information relating to the sample tube provided to the patient may also be received by the patient registration module 509 and the sample tube and collected biological sample may be registered to the patient. The provider, upon collection of the biological sample may place the sample tube into a rack before transfer to the destination lab for processing. The patient registration module may also associate the rack holding the sample tube with the patient record.

Figure 6:
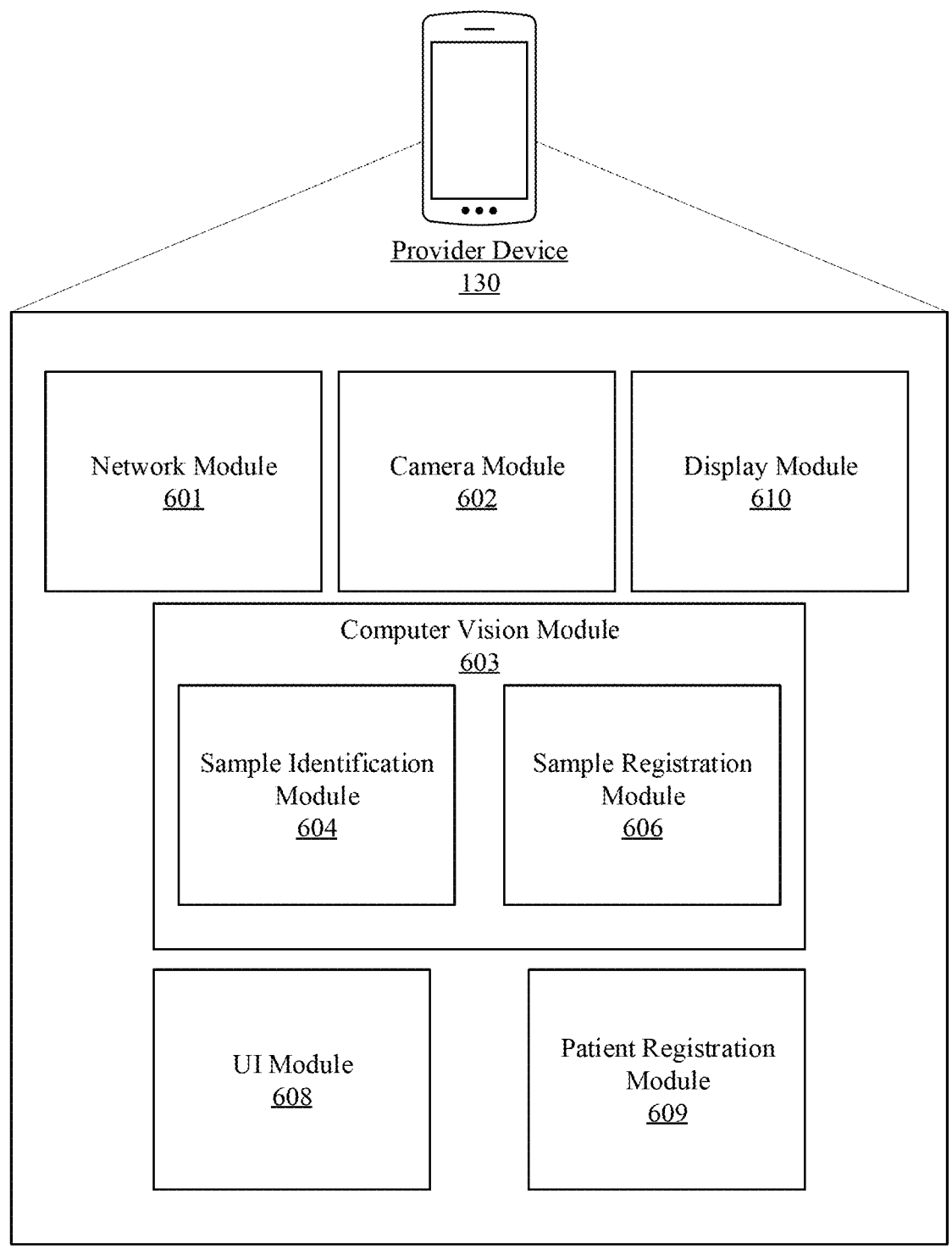
FIG. 6 is a diagram illustrating an exemplary provider device in accordance with aspects of the present disclosure.

FIG. 6 is a diagram illustrating an exemplary provider device 130 in accordance with aspects of the present disclosure. Provider device 130 may comprise a network module 601, camera module 602, computer vision module 603, sample identification module 604, sample registration module 606, UI module 608, patient registration module 609 and display module 610.

The network module 601, computer vision module 603, sample identification module 604, sample registration module 606, UI module 608, patient registration module 609 and display module 610 may be similar in function to that of network modules 301 and 501, computer vision modules 303 and 503, sample identification modules 304 and 504, sample registration modules 306 and 506, UI module 508, patient registration module 509 and display modules 203 and 510 and therefore not described in detail for sake of brevity.

Camera module 602 may comprise any camera or combination of cameras configured to record images. The cameras may be any type of image sensor which provides an image of a scene viewed from the viewpoint of the device, or user, or both. The cameras may be any device configured to detect visible light (e.g. CCD or CMOS based cameras) or light of other spectrums (e.g. multi-spectral or hyper-spectral cameras), such as infrared, ultraviolet, x-rays or any other wavelength the device is capable of detecting. Other types of cameras are possible as well, such as a time-of-flight camera, stereoscopic cameras or other camera combinations capable of determining depth of a captured image/video. The camera module 602 may include hardware, or software, or both, to enable the use of structured light depth determination or time-of-flight depth determination. Camera module 602 may also be a combination of two or more of the devices described above.

Figure 7:
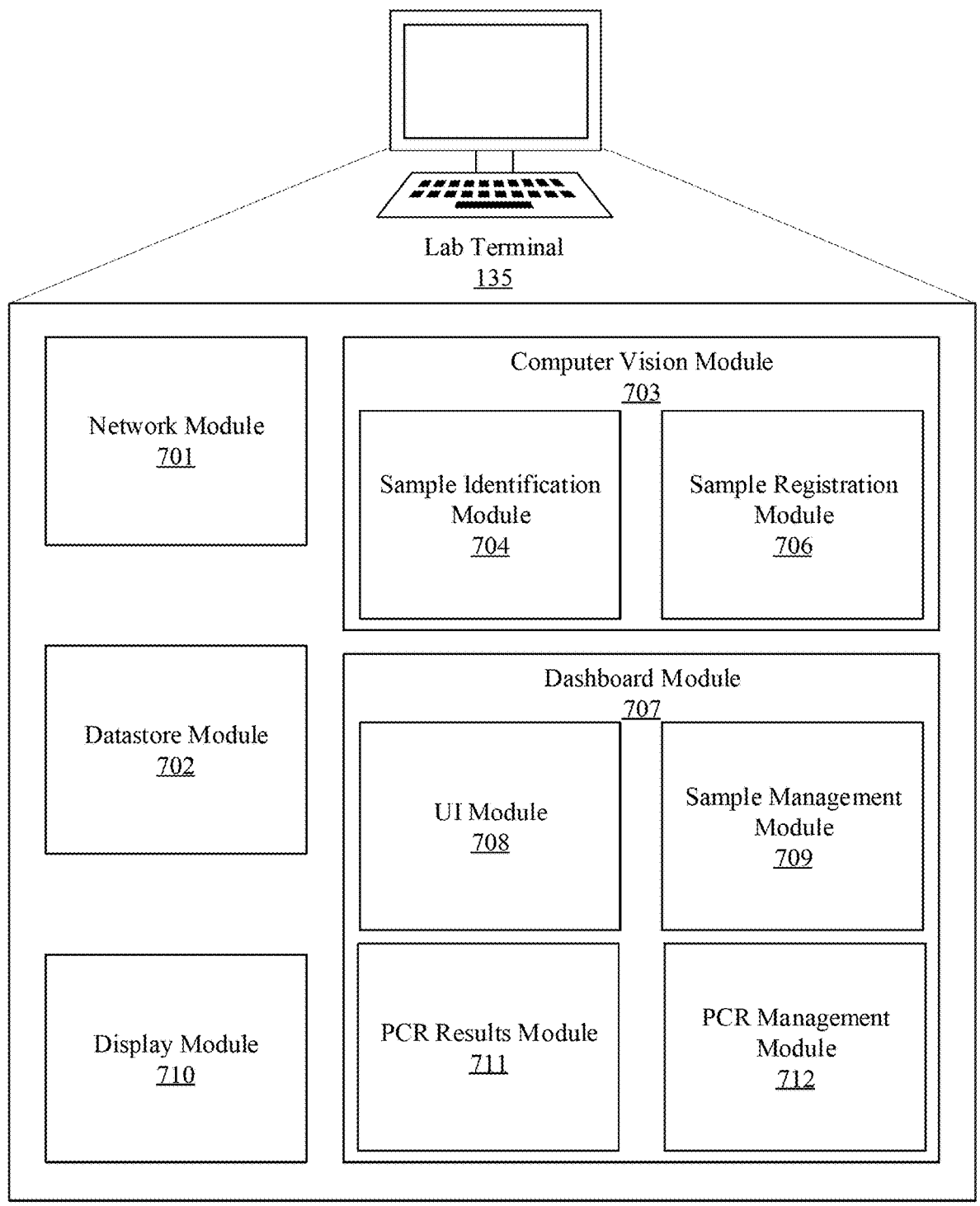
FIG. 7 is a diagram illustrating an exemplary lab terminal in accordance with aspects of the present disclosure.

FIG. 7 is a diagram illustrating an exemplary lab terminal 135 in accordance with aspects of the present disclosure. Lab terminal 135 may comprise network module 701, datastore module 702, computer vision module 703, sample identification module 704, sample registration module 706, dashboard module 707, UI module 708, sample management module 709, display module 710, PCR results module 711 and PCR management module 712.

The network module 701, datastore module 702 computer vision module 703, sample identification module 704, sample registration module 706 and display module 710 may be similar in function to that of network module 501, datastore module 502, computer vision module 503, sample identification module 504, sample registration module 506 and display module 510 and therefore not described in detail for sake of brevity.

Dashboard module 707 may comprise UI module 708, sample management module 709, PCR results module 711 and PCR management module 712. The dashboard module 707 may manage display of UI components generated by UI module 708. A dashboard, terminal or portal may display information relating to the one or more racks received at the destination lab. The dashboard module 707 may also organize samples received as individual samples tubes holding collected samples from patients or provider facilities, samples aggregated and held in one or more racks, and samples received in bags or other containers from one or more provider facilities.

Sample management module 709 may receive manifest or other information relating to the racks, sample tubes, patients, and batches of samples received at the destination lab. Upon receiving the one or more racks of samples from one or more provider facilities, the lab tech may scan each rack to verify the receipt of the sample batch. Sample management module, may update status and progress information for each received sample. After transferring samples from each rack to a sample plate, the sample management module may register the samples to the specific sample plate and to the PCR run processed for that plate.

The PCR results module 711 may retrieve, format and display the results on the display 710. The PCR results module may also send and receive results for each sample and each rack to the provider terminal 125.

PCR management module 712 may control the PCR machine itself. The PCR management module may initiate the processing of one or more plates after having the samples transferred from the racks. One or more plates may be loaded or queued to be loaded and processed by one or more PCR machines. The PCR management module may also transfer the PCR results from the PCR machine to the analysis server 115.

Figure 8:
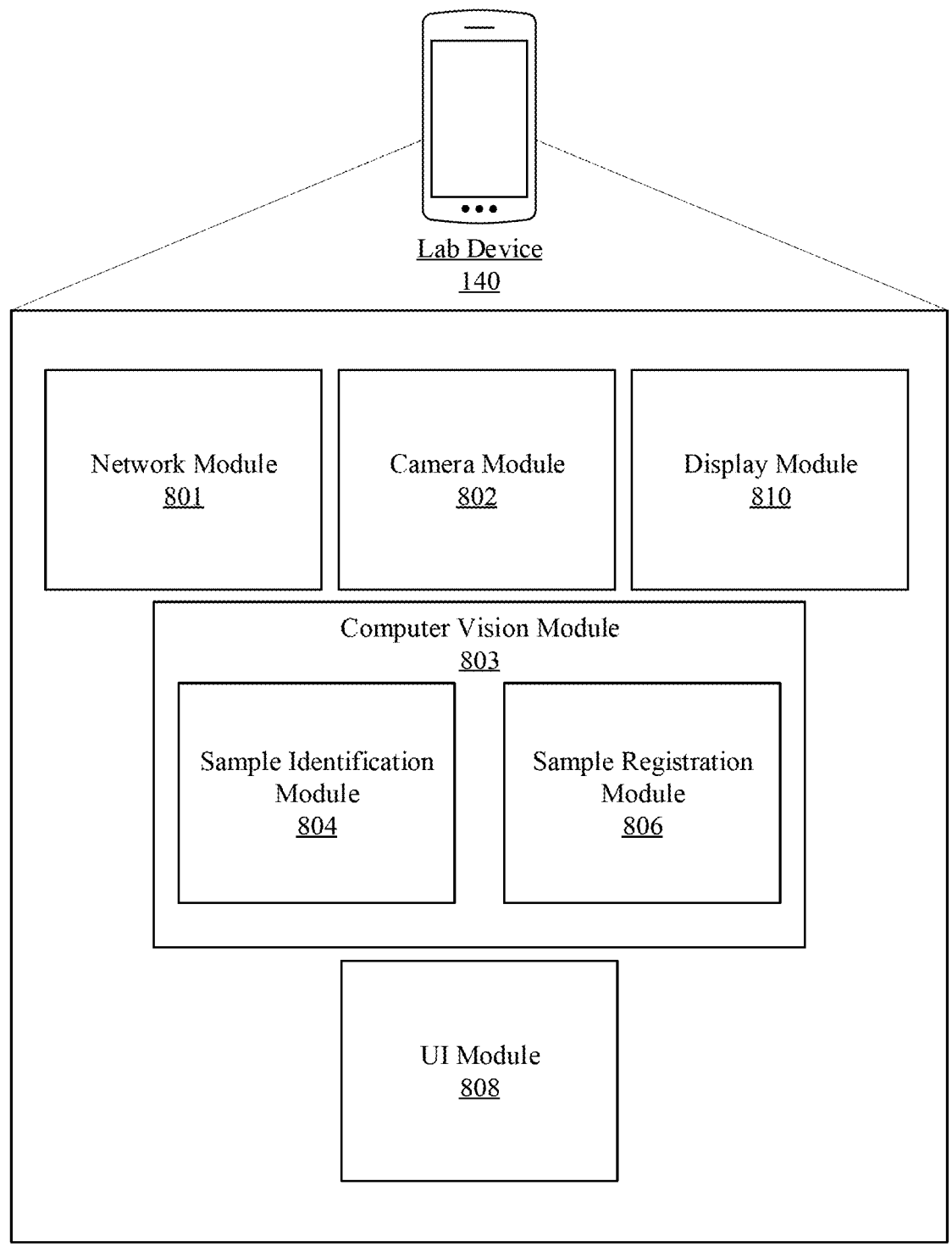
FIG. 8 is a diagram illustrating an exemplary lab device in accordance with aspects of the present disclosure.

FIG. 8 is a diagram illustrating an exemplary lab device in accordance with aspects of the present disclosure.

The network module 801, camera module 802, computer vision module 803, sample identification module 804, sample registration module 806, UI module 808 and display module 810 may be similar in function to that of network module 701, camera module 602, computer vision module 703, sample identification module 704, sample registration module 706, UI module 708 and display module 510 and therefore not described in detail for sake of brevity.

FIGS. 9A-9G are diagrams illustrating an exemplary tube rack and rack cover in accordance with aspects of the present disclosure. Tube rack 900 may comprise a rack control blank 901 and receptacles for one or more sample tubes 902. Rack 900 may be of any dimension that corresponds to the dimensions of the sample trays for which the samples are to be transferred to. The rack may be 3D printed, injection molded or otherwise manufactured from plastic or resins. Bioplastics and compostable materials as well as composite materials may also be used in the construction of the rack 900 and rack cover 905. A rack cover 905 may fit over or around the rack to protect the sample tubes during transport or storage. The rack may also be designed to slide into an enclosure. Covers and enclosures may also be designed to carry and store multiple racks at one time. There may be individual shelves used to hold each individual rack or an opening may be large enough to hold a plurality of racks stacked on one another. The racks may also include recesses and protrusions on the top and bottoms of the racks to allow for the racks to be securely stacked. The underside of each rack may also comprise regions designed to secure sample tubes of the rack below. For example, the bottom of each rack may have a circular indention which matches the sample tube lid, allowing for each sample to be secured by the rack stacked on top of them.

Figure 9A:
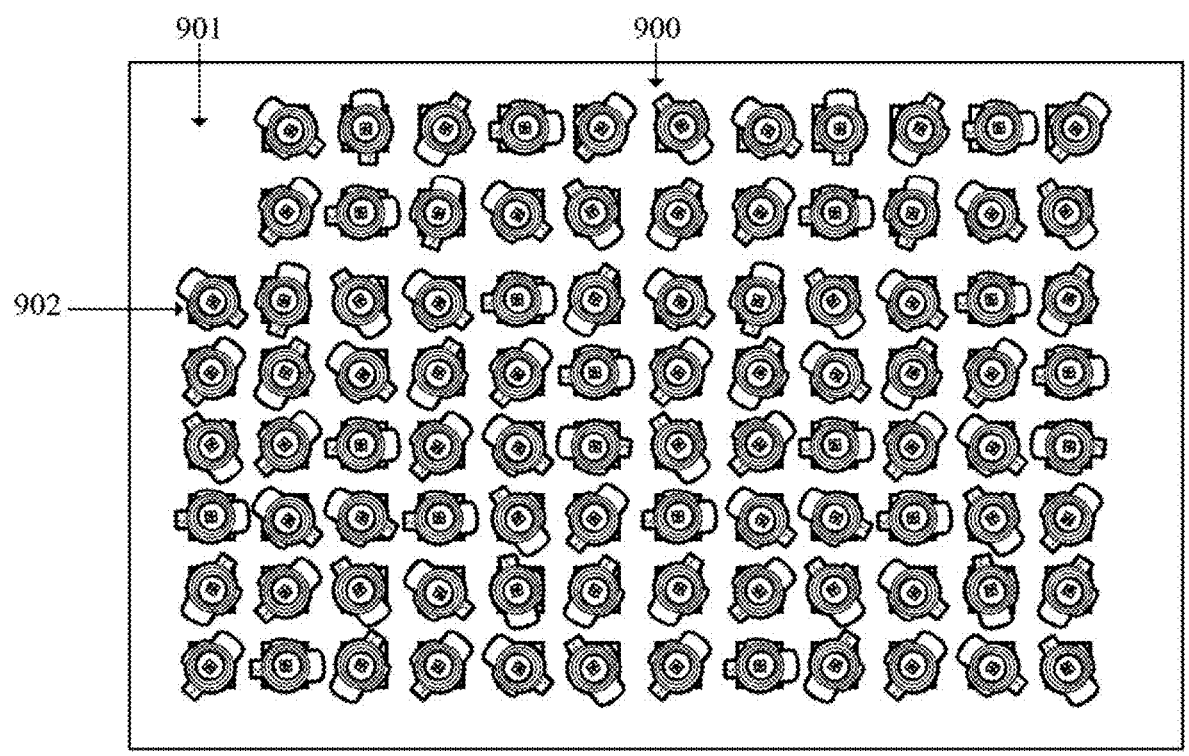
FIG. 9A is a diagram illustrating an exemplary tube rack in accordance with aspects of the present disclosure.
Figure 9B:
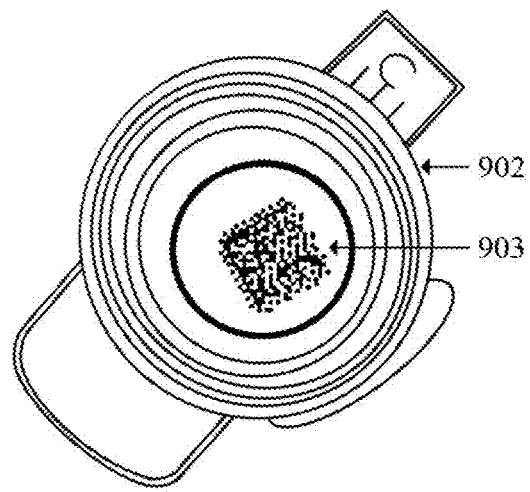
FIG. 9B is a diagram illustrating an exemplary sample tube in accordance with aspects of the present disclosure.
Figure 9C:
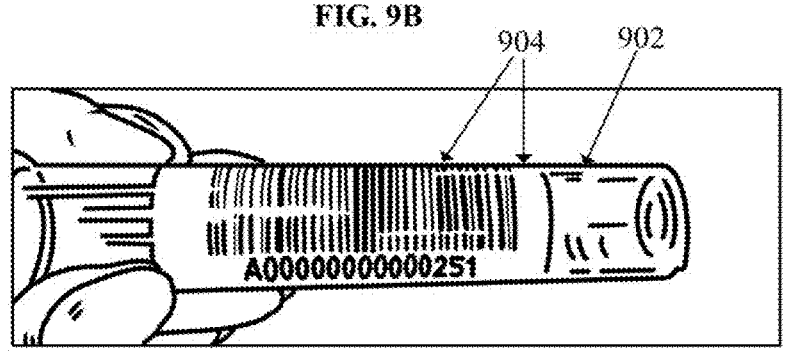
FIG. 9C is a diagram illustrating an exemplary sample tube in accordance with aspects of the present disclosure.

Sample tube 902 may be any sample tube with dimensions that fit into the slots or rack 900. FIG. 9B is a diagram illustrating an exemplary sample tube in accordance with aspects of the present disclosure. Sample tube 902 may have a QR code printed on the affixed lid. The QR code may be used by the provider device 130 and lab device 140 in the identifying, scanning, registration and verification of samples held in the racks 900. As shown in FIG. 9C, sample tube 902 may also include a barcode and label affixed to the side of the body of the tube. This barcode may also be used by provider and lab techs to identify samples when a scan of the QR code fails.

Figure 9D:
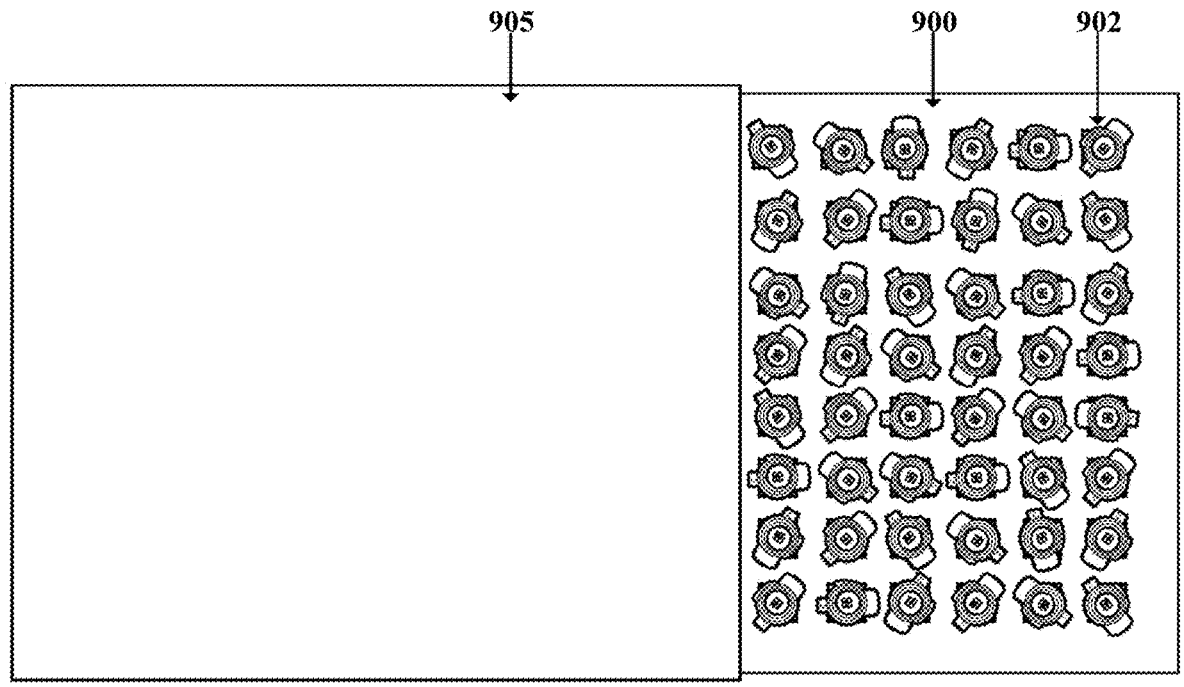
FIG. 9D is a diagram illustrating an exemplary tube rack and tube cover in accordance with aspects of the present disclosure.
Figure 9E:
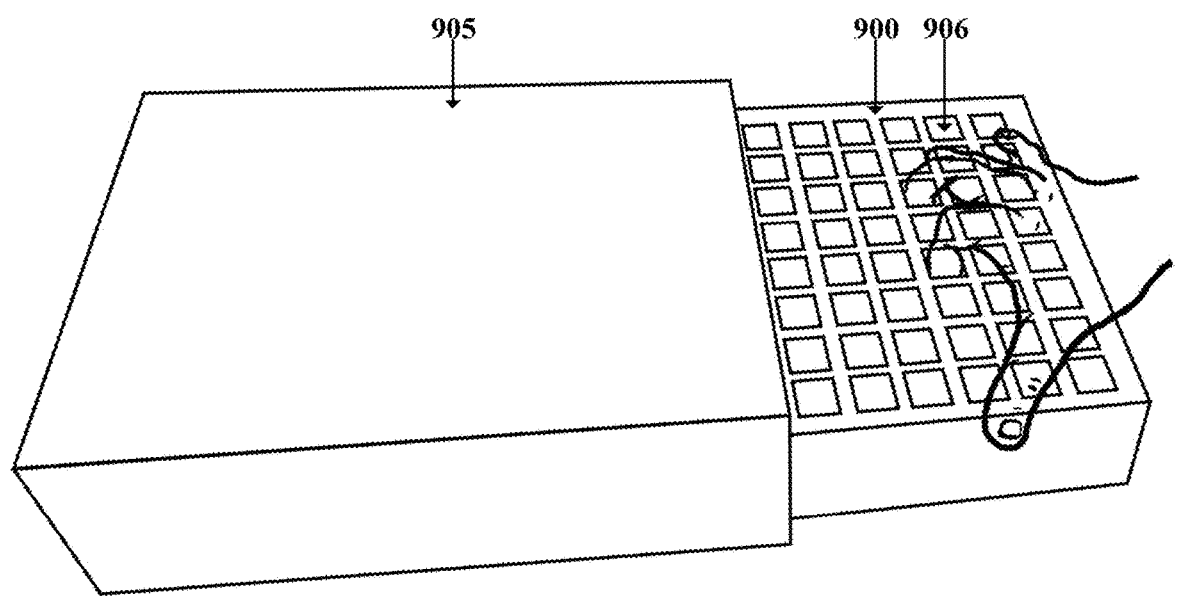
FIG. 9E is a diagram illustrating an exemplary tube rack and tube cover in accordance with aspects of the present disclosure.

FIG. 9D is an overhead view of a rack 900 partially inserted into rack cover 905. Rack 900 is shown with sample tubes 902 inserted into all available slots. FIG. 9E shows a perspective view of an empty rack 900 being slid into rack cover 905. Slots 906 are shown as square, but may also be of any other shape, such as circular.

Figure 9F:
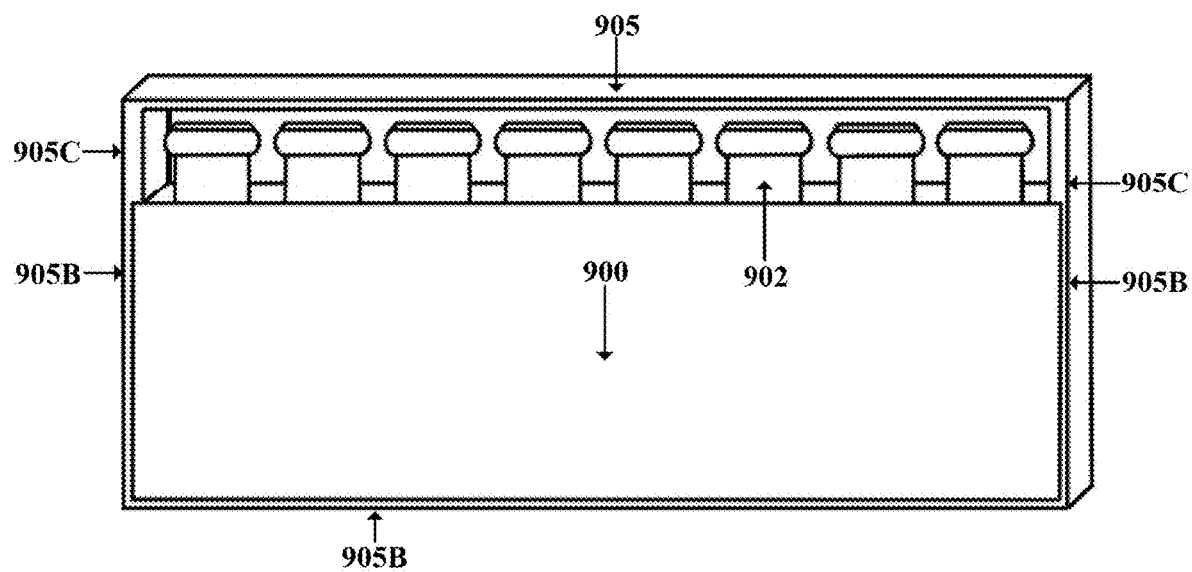
FIG. 9F is a diagram illustrating an exemplary tube rack and tube cover in accordance with aspects of the present disclosure.
Figure 9G:
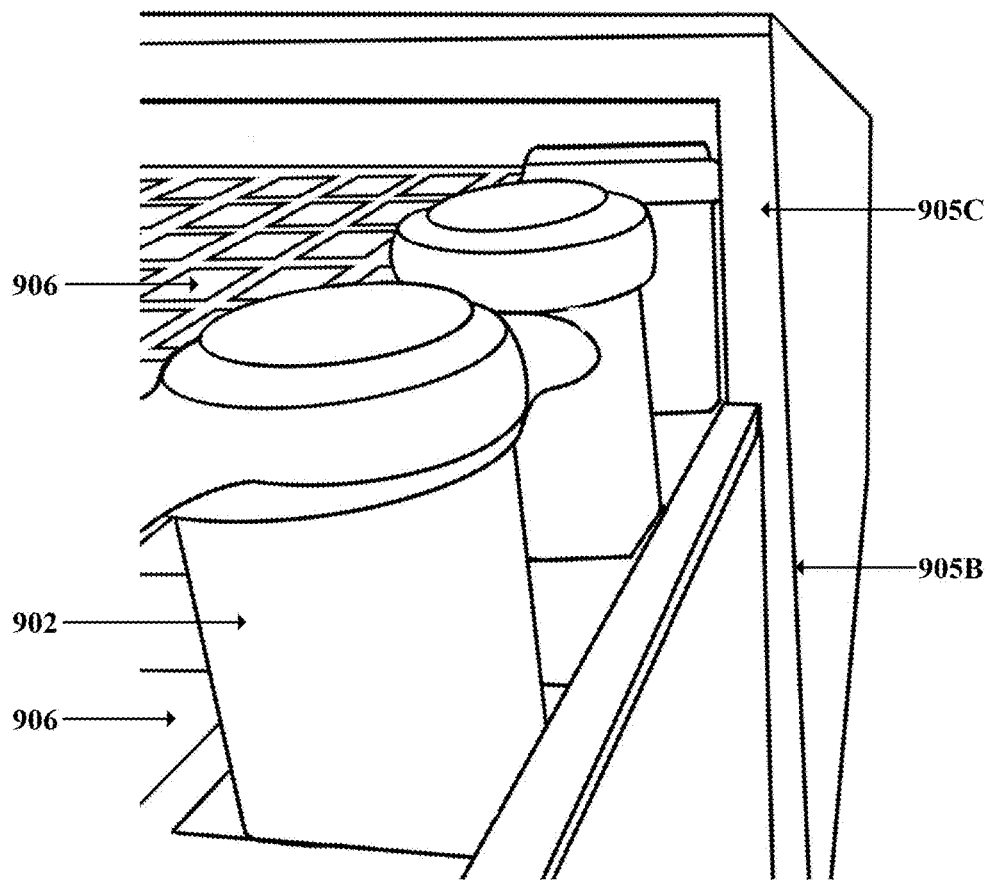
FIG. 9G is a diagram illustrating an exemplary tube rack and tube cover in accordance with aspects of the present disclosure.

FIGS. 9F and 9G show a diagram from a frontal view of the rack 900 and rack cover 905. The rack cover may comprise regions of differing thicknesses 905B and 905C. The difference in thicknesses between 905B and 905C in effect creates a channel/rail/slide for the rack 900 to slide into the cover and be retained once fully inserted. The thickness of the sliding channel 905B may be a thickness which allows for the rack 900 to slide without resistance at the opening end of the rack cover 905, and increase at the back to increase the resistance when the rack 900 has been fully inserted into the rack cover 905. The guiding channel 905C may have a thickness greater than that of the sliding channel 905B thickness. The thickness of the guiding channel 905C may be uniform from the opening of the rack cover 905 to the very back of the cover. The height of the guide channel 905C may increase from the opening of the rack cover 905 to the back of the cover. Similarly to the sliding channel 905B, the guide channel 905C may be dimensioned so as to provide little to no resistance at the opening of the rack cover 905 when a rack 900 is being inserted and increasing the resistance on the rack 900 when fully inserted. This may be accomplished by increasing the size of the guide channel 905C. For example, the length from the top of the rack cover to the bottom of the guide channel 905C may be 2.5 cm at the opening of the cover, but may increase to 2.6 cm. This increase may cause the rack 900 to be gripped by the cover and held in place by the friction between the rack 900 and the guide channel 905C. The friction locking of the rack 900 may be accomplished in the same manner by increasing the thickness of the sliding channel 905B, from the opening to the back end of the rack cover 905. The sliding channel 905B may also be narrowed from the opening to the back of the cover while maintaining the same thickness. The narrowing or thickening of the slide channels 905B may be uniform from the opening to the back of the rack cover 905. The narrowing or thickening of the slide channels 905B may also be non-uniform and increased only within a predetermined distance from the end of the rack cover 905. For example, the dimensions of the slide channel 905B may be maintained for the majority of the length of the rack cover 905. This would allow for the rack 900 to be inserted and slid into the rack cover 905 with little or no friction/resistance until it reaches a position close to the end of the cover. Upon reaching the predetermined position in the rack cover 905, the slide channel may narrow or thicken at a constant rate until the end, at logarithmic rate, at a linearly incremental rate, exponential rate or other desired rate of increase of thickness or narrowing of the slide channel 905B.

The rack cover 905 may also have one or more protrusions which may force the rack up and into contact with the guide channel 905C. One or more protrusions on the top surface of the bottom portion of the rack cover 905 may have corresponding indentions on the bottom of the rack 900. When slid into the rack cover 905, the protrusions may engage the intentions and lock the rack 900 in place. The protrusions may alternatively be positioned on the underside of the guide channel and the corresponding indentions positioned on the top of the rack 900.

The locking of the rack 900 into the rack cover 905 may be accomplished by one or more of the above described locking mechanisms, alone or in combination.

In example, the test tub rack includes a solid rack body for example made of a hard plastic or other suitable material. The rack body may for example be 3D printed. The rack body has a bottom surface and a top surface with four side walls connecting the top and bottom surfaces, thereby forming an enclosure with a hollow interior. The top surface includes multiple columns and rows of openings disposed in the top surface of the rack body. The openings, for example, may be in different shapes such as a square or circle or other suitable shape which are configured to receive a test tube or vial. In one example, each of the multiple columns have an equal number of openings, and at least one column has two fewer openings than the other multiple columns. In one example, the rack 900 has multiple columns with at least 8 openings, and at least one column with at least 6 openings configured to receive a vial or test tube. In another example, the rack has two rows with 11 openings, and the other rows have 12 openings configured to receive a vial or test tube. The rack also may include a cover 905 which is solid and may be removeably attached to the rack. The cover 905 when secured to the rack encloses the vials or test tubes placed within the openings. This allows the rack 900 with the vials or test tubes to be secured and safely transported. In one example, the rack 900 has 94 openings for receiving the vials or test tubes. The rack may 900 be configured with fewer or greater number of rows and columns to adjust the quantity or available openings for the placement of vials or test tubes.

Figure 10A:
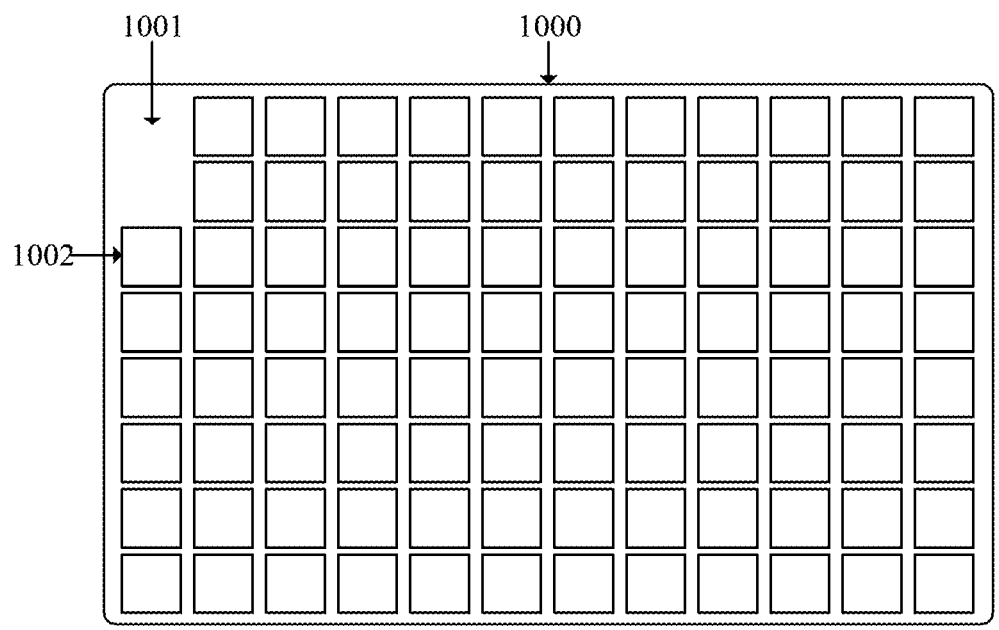
FIG. 10A is a diagram illustrating an exemplary tube rack in accordance with aspects of the present disclosure.

FIG. 10A is a diagram illustrating an exemplary tube rack 1000 in accordance with aspects of the present disclosure. Tube rack 1000 may comprise a rack control blank region 1001 and sample tube cells/receptacles 1002. The rack control blank region may be marked or otherwise distinguished from other parts of the rack. The area may also be left blank and without a sample cell to indicate that the corresponding sample wells of the sample plate are reserved for positive control and negative control samples. The rack control blank region 1001 provides a landmark for determining orientation and positioning of the racks when capturing images of the rack and sample tubes held by the rack. This may greatly help in the identifying of sample tubes in the captured image and the drawing of bounding boxes around the sample tube regions to be extracted and analyzed.

Figure 10B:
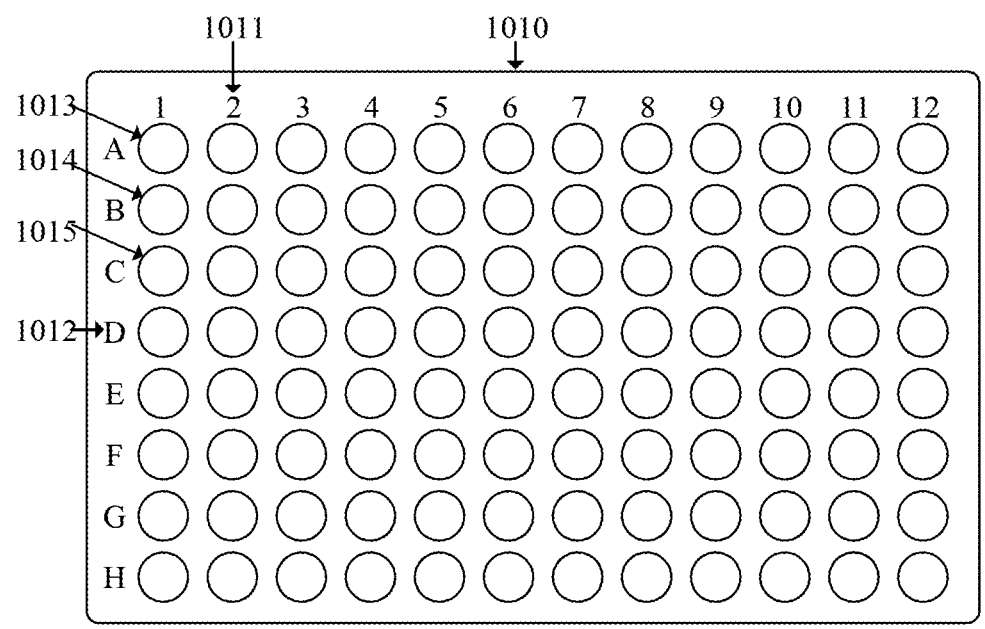
FIG. 10B is a diagram illustrating an exemplary sample tray in accordance with aspects of the present disclosure.

FIG. 10B is a diagram illustrating an exemplary sample tray 1010 in accordance with aspects of the present disclosure. sample tray 1010 may comprise tray columns 1011, tray rows 1012, positive control sample 1013, negative control sample 1014 and first test sample 1015.

Figure 11:
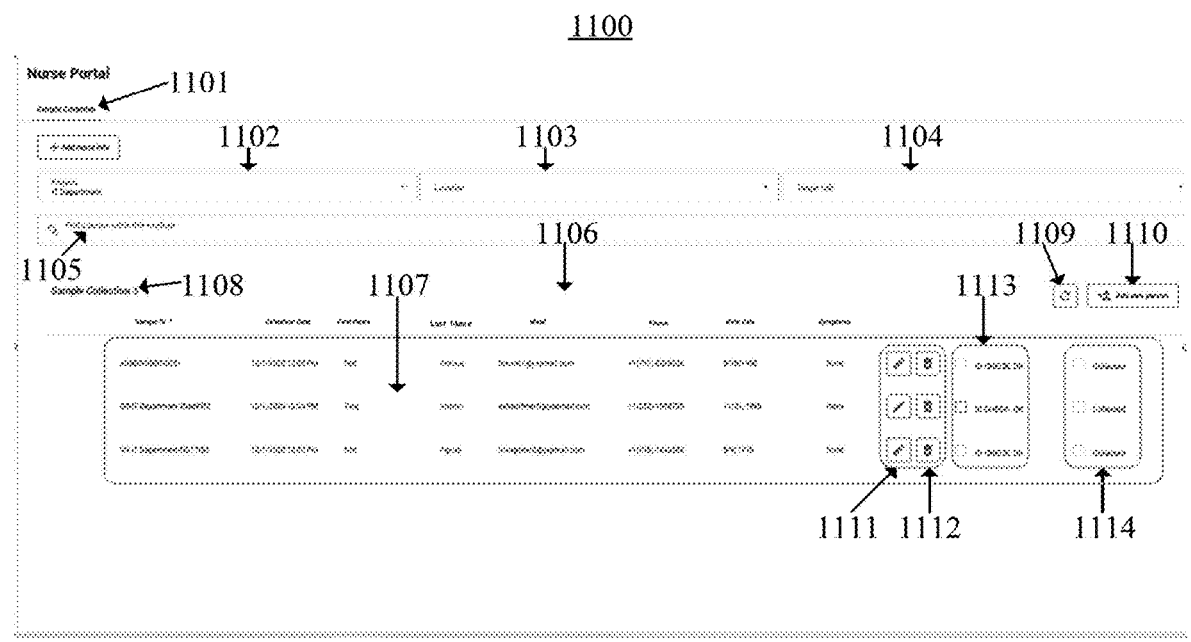
FIG. 11 is a diagram illustrating an exemplary nurse portal in accordance with aspects of the present disclosure.

FIG. 11 is a diagram illustrating an exemplary nurse portal 1100 in accordance with aspects of the present disclosure. Nurse portal 1100 may comprise sample collection interface 1101, project selection menu 1102, location selection menu 1103, target lab selection menu 1104, patient search field 1105, patient entry pane 1106, patient list 1107, patient count indicator 1108, patient list refresh button 1109, add patient button 1110, edit patient button 1111, delete patient button 1112, ID verification check 1113 and patient sample collection check 1114.

The sample collection interface 1101 may be generated by the dashboard module 507 or UI module 508 of provider terminal 125. The sample collection interface 1101 comprises multiple selection menus and one or more textual search fields. During check-in and registration of patients, a provider may use the nurse portal to enter the patient into the system and register samples and sample tubes to the patient. The provider may select, from a project selection menu 1102, a project for which the patient is associated with. The provider may also selection a location from a location selection menu 1103 and the lab for which the samples are to be processed from a target lab selection menu 1104. The provider may enter a patients name or other identifying information into the patient search field 1105 to retrieve records for the patient.

The patient entry pane 1106 may display a patient list 1107 and patient count indicator 1108. Patients may be added to the list through selection of the add patient button 1110. At any time, the provider may refresh the patient list by selecting the patient list refresh button 1109. Patient records listed in the patient list may be selected updated or edited. The provider may edit any field for a patient by selecting the edit patient button 1111. Records may also be deleted by selecting the delete patient button 1112 associated with the patient to be deleted/removed from the current list. An ID verification check 1113 may be used for validation of user identity before a sample may be collected or processed. The provider may place a check in the ID verification check 1113 to verify that the provider checked the ID of the patient. The patient sample collection check 1114 may be used to identify which patients have completed the sample collection process and which samples are ready to be aggregated and transferred to the destination lab.

Figure 12:
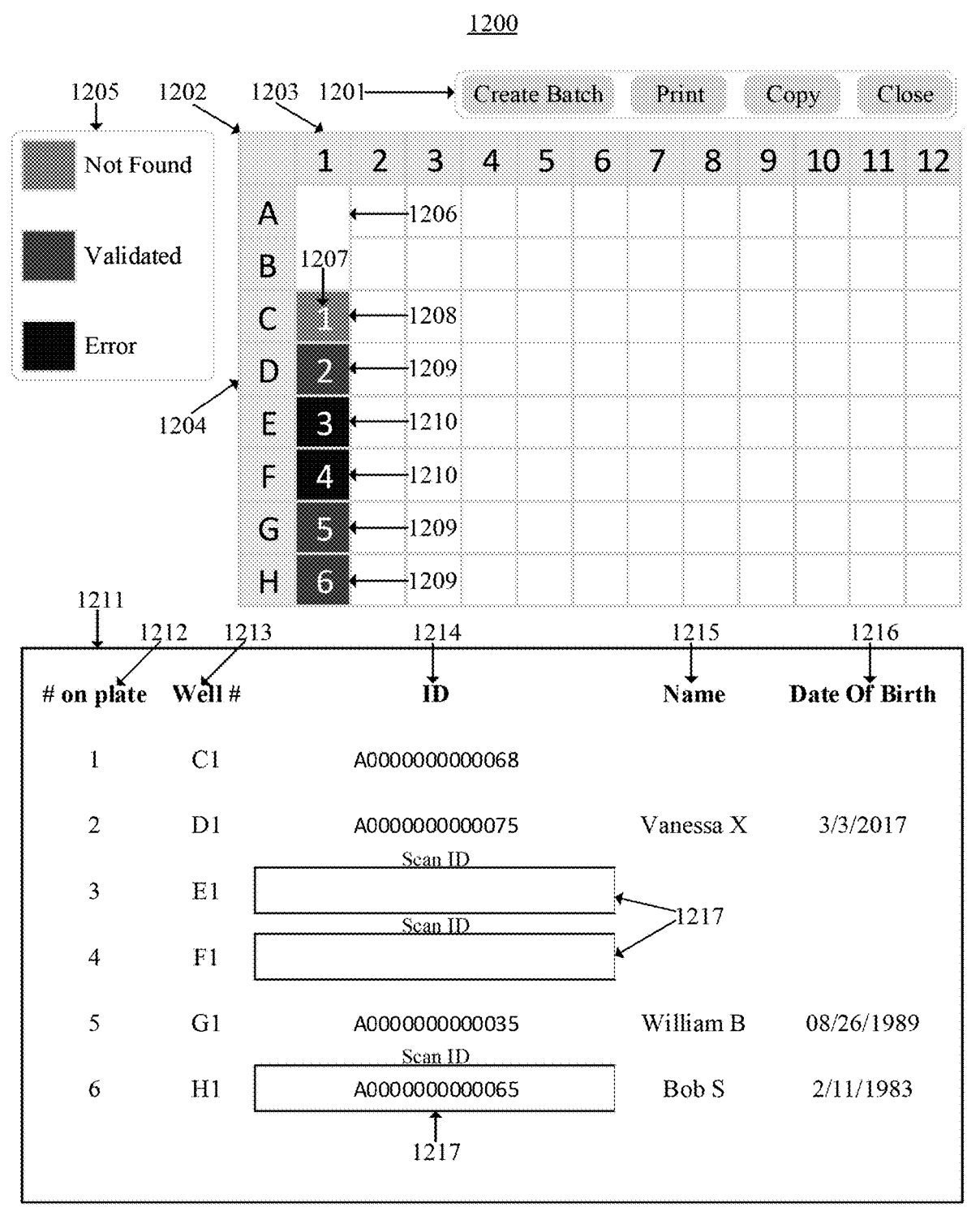

FIG. 12 is a diagram illustrating an exemplary rack management interface 1200 in accordance with aspects of the present disclosure. Rack management interface 1200 may comprise rack management menu 1201, rack visualization 1202, rack columns 1203, rack rows 1204, rack key 1205, rack control blank 1206, sample number 1207, not found sample 1208, validated sample 1209, missing sample 1210, rack information pane 1211, number on plate 1212, well grid number 1213, sample ID 1214, patient name 1215, patient DOB 1216 and scan ID field 1217.

Rack management menu 1201 may provide menu options for a provider or lab tech to create a new batch, print the rack information pane 1211 for the current batch being viewed, as well as copy and close the batch. The provider or lab tech may have the option to print the rack visualization 1202, the rack information pane 1211 or both. The rack visualization 1202 may display a visual representation of the rack and the sample tubes held in the rack. Upon capturing one or more images of the rack, the rack visualization 1202 may display in each cell an indication of sample tube identification and the associated sample tube position in the rack. The status of sample tube identification may be marked by highlighting the corresponding cell in a predetermined color. Rack key 1205 displays the different cell colors used to indicate "Not Found," "Validated" and "Error." An additional color may be used to indicate cells that are empty after the last filled cell. The rack visualization may display a rack control blank 1206 in the region corresponding to the sample plate wells for control positive and control negative samples. The sample number 1207 may be used to provide a reference to the sample entries in rack information pane 1211. Cell "1" is classified as "Sample Not Found" 1208, cells "2," "5" and "6" are classified as "Validated Sample" 1209 and cells "3" and "4" are classified as "Missing Sample" 1210. If a sample is either classified as "Sample Not Found" 1208 or "Missing Sample" 1210, the rack may need to be imaged/scanned again. In some embodiments, individual cells may be scanned for samples that are classified as "Sample Not Found" 1208 or "Missing Sample" 1210. "Sample Not Found" 1208 may be a result of an incorrect reading of the QR code or there being no corresponding sample record associated with the rack or batch, or possibly a sample that did not receive an initial scan to register it with a patient. For example, the system may evaluate the captured images and determine that a test tube is missing from a location in the rack and identify that location as a missing sample, or sample not found. In another example, the system may evaluate the captured images and may not be able to read a QR code (for example, a smudge or unreadable graphical image), and note that the location with an indication of an error. In another example, the system may be able to read the QR code, but for some reason the identifier may not be in a database, and may indicate the location as not found. This may occur for example, if an unregistered test tube was placed in the rack.

Rack information pane 1211 may comprise the number on plate 1212, well grid number 1213, sample ID 1214, patient name 1215, patient DOB 1216 and scan ID field 1217. The number on plate 1212 may correspond to the sample number 1207 that is to be transferred from the rack to a well in the sample plate. The well grid number 1213 displays the coordinates of the sample in a row/column format. The sample ID 1214, patient name 1215 and patient DOB 1216 are retrieved upon successful identification and registration of a sample tube. When a sample ID is unable to be identified from the captured images, the provider or lab tech may be provided with an option to scan the barcode or QR code of each individual tube in which an ID was unable to be determined.

Figure 13:
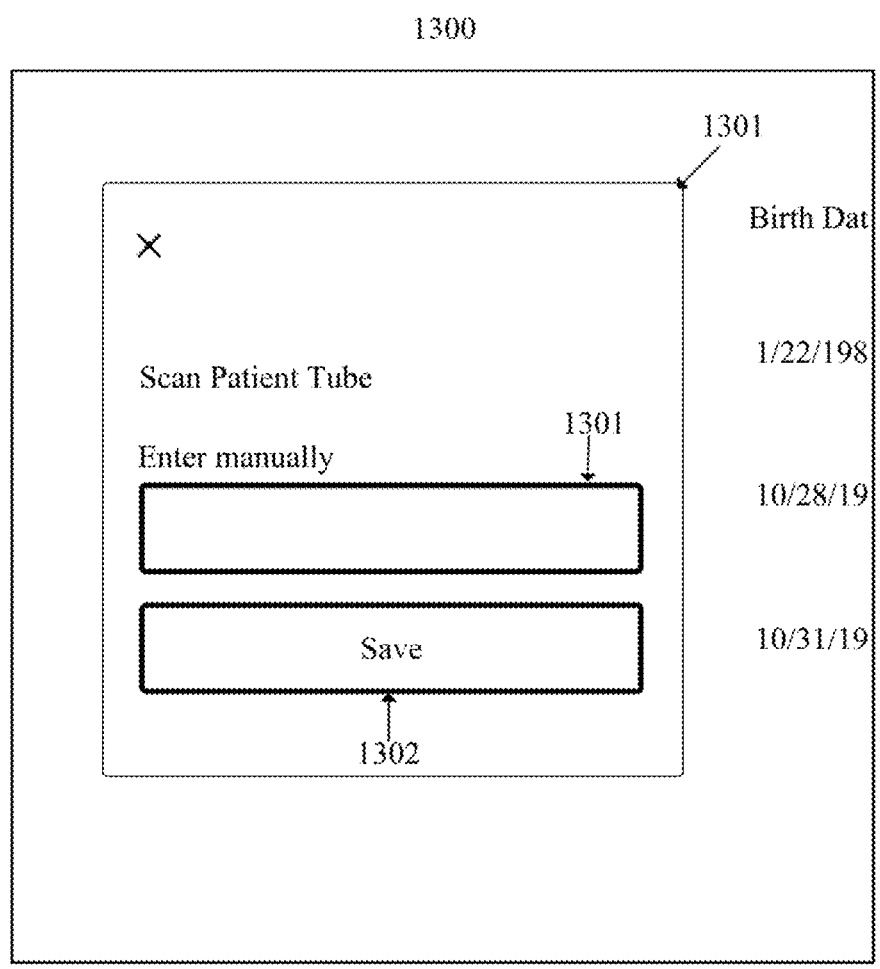
FIG. 13 is a diagram illustrating an exemplary individual sample entry window in accordance with aspects of the present disclosure.

FIG. 13 is a diagram illustrating an exemplary individual sample entry window 1300 in accordance with aspects of the present disclosure. Individual sample entry window 1300 may comprise sample ID 1301 and a save sample button 1302. If a sample is unable to be identified from images captured of the rack, the provider or lab tech may be provided with a prompt similar to FIG. 13. The provider or lab tech may capture an image of the barcode or QR code of the sample tube in an attempt to correctly read the ID information of the sample tube. The provider or lab tech may also use a barcode reader or other optical/laser scanning device to read the ID information from the sample tube. The provider or lab tech may also be allowed to manually type in the ID information printed on the ID label if the barcode and QR code are unreadable.

Figure 14:
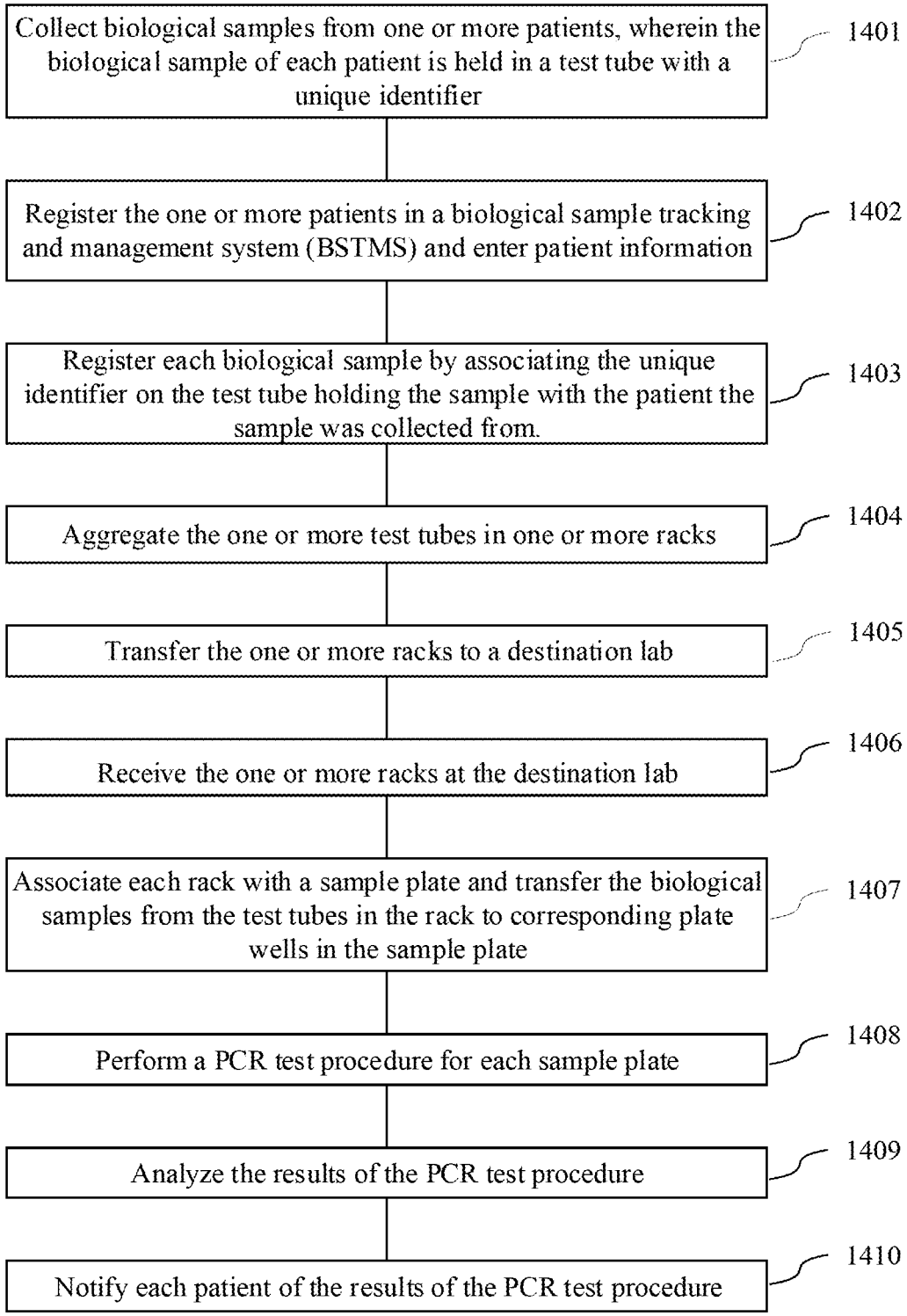
FIG. 14 is a flow chart illustrating an exemplary method that may be performed in accordance with some embodiments.

FIG. 14 is a flow chart illustrating an exemplary method 1400 that may be performed in accordance with some embodiments.

At step 1401, the method comprises collect biological samples from one or more patients, wherein the biological sample of each patient is held in a test tube with a unique identifier.

At step 1402, the method comprises register the one or more patients in a biological sample tracking and management system (BSTMS) and enter patient information.

At step 1403, the method comprises register each biological sample by associating the unique identifier on the test tube holding the sample with the patient the sample was collected from.

At step 1404, the method comprises aggregate the one or more test tubes in one or more racks.

At step 1405, the method comprises transfer the one or more racks to a destination lab.

At step 1406, the method comprises receive the one or more racks at the destination lab.

At step 1407, the method comprises associate each rack with a sample plate and transfer the biological samples from the test tubes in the rack to corresponding plate wells in the sample plate.

At step 1408, the method comprises perform a PCR test procedure for each sample plate.

At step 1409, the method comprises analyze the results of the PCR test procedure.

At step 1410, the method comprises notify each patient of the results of the PCR test procedure.

FIG. 15 is a flow chart illustrating an exemplary method 1500 that may be performed in accordance with some embodiments.

At step 1501, the method comprises capture one or more images of a rack, wherein the rack holds one or more test tubes and wherein each test tube holds a biological sample.

At step 1502, the method comprises analyze the one or more images to determine orientation of the rack, identify each test tube, read the QR code on each test tube and associate each test tube with a patient based on the read QR code.

At step 1503, the method comprises store information related to the rack, each test tube held by the rack and the patient associated with each test tube.

At step 1504, the method comprises transfer the rack from a provider location to a destination lab.

At step 1505, the method comprises receive the rack at the destination lab.

At step 1506, the method comprises capture one or more images of a rack and analyze the images.

At step 1507, the method comprises identify each test tube, read the QR code on each test tube and retrieve patient information based on the QR code.

At step 1508, the method comprises associate the rack with a sample plate and transfer the biological samples from the test tubes in the rack to corresponding plate wells in the sample plate.

At step 1509, the method comprises perform a PCR test procedure for each biological sample on the sample plate.

Figure 16:
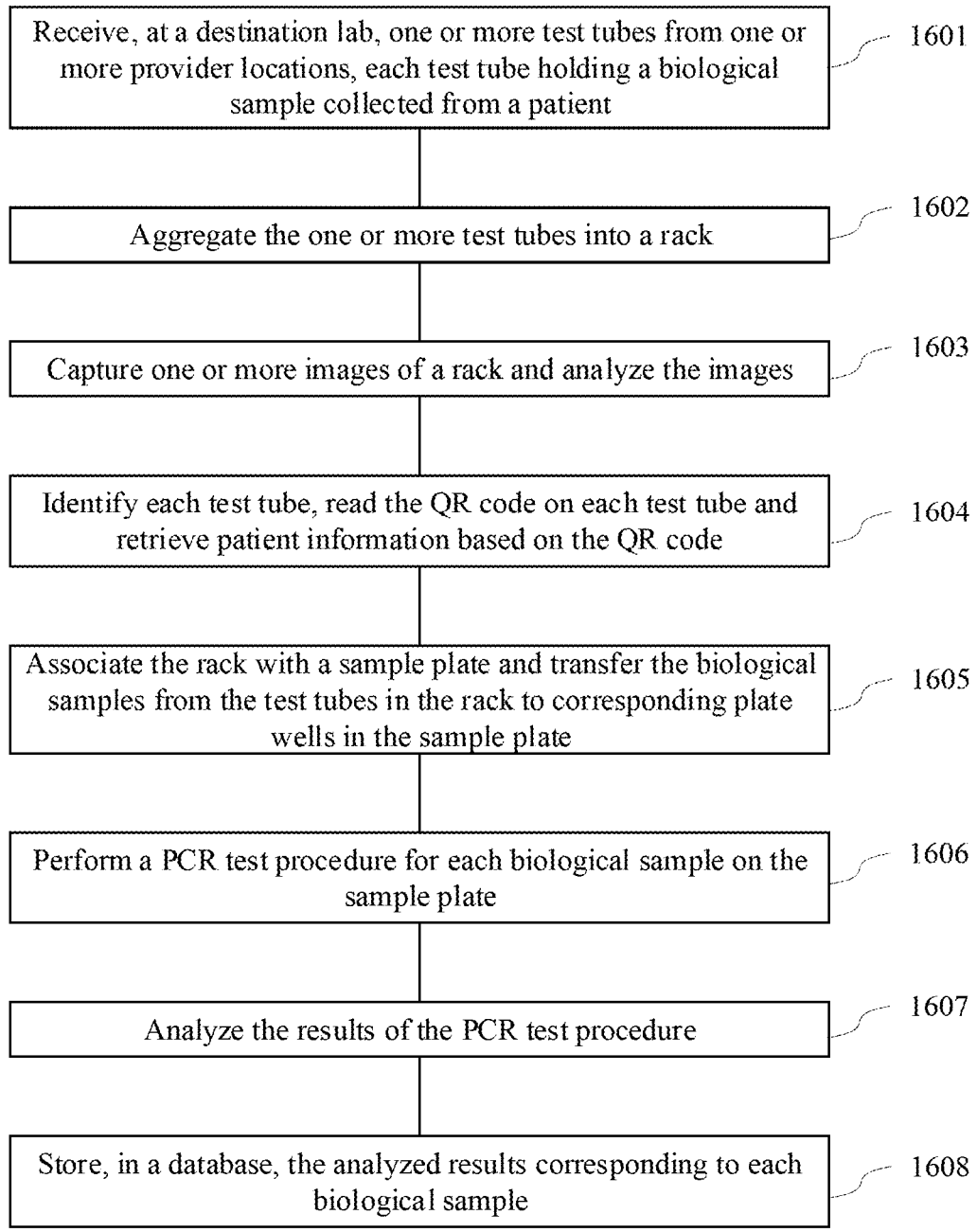
FIG. 16 is a flow chart illustrating an exemplary method that may be performed in accordance with some embodiments.

At step 1510, the method comprises analyze the results of the PCR test procedure FIG. 16 is a flow chart illustrating an exemplary method 1600 that may be performed in accordance with some embodiments.

At step 1601, the method comprises receive, at a destination lab, one or more test tubes from one or more provider locations, each test tube holding a biological sample collected from a patient.

At step 1602, the method comprises aggregate the one or more test tubes into a rack.

At step 1603, the method comprises capture one or more images of a rack and analyze the images.

At step 1604, the method comprises identify each test tube, read the QR code on each test tube and retrieve patient information based on the QR code.

At step 1605, the method comprises associate the rack with a sample plate and transfer the biological samples from the test tubes in the rack to corresponding plate wells in the sample plate.

At step 1606, the method comprises perform a PCR test procedure for each biological sample on the sample plate.

At step 1607, the method comprises analyze the results of the PCR test procedure.

At step 1608, the method comprises store, in a database, the analyzed results corresponding to each biological sample.

Figure 17:
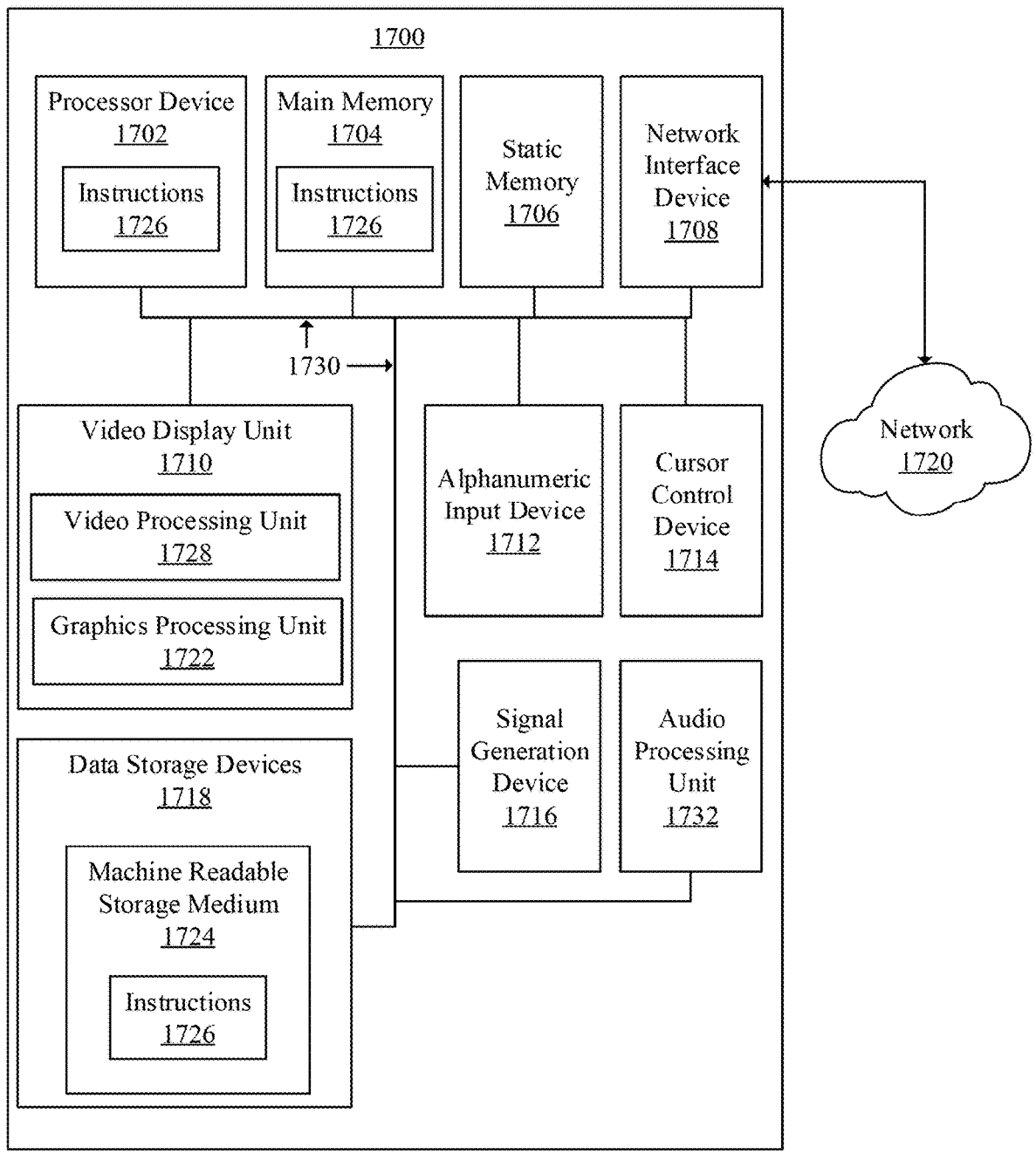
FIG. 17 is a diagram illustrating an exemplary computer that may perform processing in some embodiments and in accordance with aspects of the present disclosure.

FIG. 17 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 1700 includes a processing device 1702, a main memory 1704 (e.g., read-only memory (ROM), flash memory, dynamic random access memory (DRAM) such as synchronous DRAM (SDRAM) or Rambus DRAM (RDRAM), etc.), a static memory 1706 (e.g., flash memory, static random access memory (SRAM), etc.), and a data storage device 1718, which communicate with each other via a bus 1730.

Processing device 1702 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1702 may also be one or more special-purpose processing devices such as an application specific integrated circuit (ASIC), a field programmable gate array (FPGA), a digital signal processor (DSP), network processor, or the like. The processing device 1702 is configured to execute instructions 1726 for performing the operations and steps discussed herein.

The computer system 1700 may further include a network interface device 1708 to communicate over the network 1720. The computer system 1700 also may include a video display unit 1710 (e.g., a liquid crystal display (LCD) or a cathode ray tube (CRT)), an alphanumeric input device 1712 (e.g., a keyboard), a cursor control device 1714 (e.g., a mouse), a graphics processing unit 1722, a signal generation device 1716 (e.g., a speaker), graphics processing unit 1722, video processing unit 1728, and audio processing unit 1732.

The data storage device 1718 may include a machine-readable storage medium 1724 (also known as a computer-readable medium) on which is stored one or more sets of instructions or software 1726 embodying any one or more of the methodologies or functions described herein. The instructions 1726 may also reside, completely or at least partially, within the main memory 1704 and/or within the processing device 1702 during execution thereof by the computer system 1700, the main memory 1704 and the processing device 1702 also constituting machine-readable storage media.

In one implementation, the instructions 1726 include instructions to implement functionality corresponding to the components of a device to perform the disclosure herein. While the machine-readable storage medium 1724 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A system for tracking and managing biological samples, the system comprising:
   a rack apparatus configured to hold one or more biological sample containers, the rack apparatus comprising a plurality of columns and rows of rack openings disposed in a top portion of the rack apparatus, wherein at least one of the plurality of columns comprises a control blank region having two fewer rack openings than the other plurality of columns, and wherein the other plurality of columns of the rack apparatus have an equal number of rack openings and wherein the rack openings are positioned asymmetrically; and
   a software component comprising one or more modules configured to perform, when executed by one or more processors, operations comprising:
   capturing, by a camera module, one or more images of a top portion of one or more biological sample containers positioned in the rack apparatus;
   wherein the top surface of a biological sample container includes a graphical identifier representing an identifier with a respective biological sample held within a container;
   identifying, via the one or more processors, the control blank region in the one or more captured images;
   determining, via the one or more processors and based at least in part on the identifying of the control blank region, an orientation of the rack in the one or more captured images;
   determining, via the one or more processors and based on the orientation of the rack, a position in the rack apparatus of each biological sample container;
   generating, via the one or more processors and based on the determined orientation, a bounding box around each of the one or more biological sample containers in the one or more captured images;
   analyzing, via the one or more processors, a region contained within each bounding box in the one or more captured images;
   identifying, via the one or more processors and based on analyzing of the region of each bounding box, one or more identifiers in the one or more captured images;
   associating, via the one or more processors, each identifier with the determined position;
   registering, via the one or more processors, each of the one or more biological sample containers with a sample record, wherein the registration is based on the identified identifier; and
   storing in a database, the sample record of each of the one or more biological samples.

2. The system of claim 1, wherein the one or more biological sample containers are filled with biological samples collected from one or more patients at a second location, wherein the second location are and the first location are different.

3. The system of claim 2, wherein the graphical identifier on the top portion of the biological sample container is a QR code or a bar code representing a patient identifier.

4. The system of claim 2, wherein the rack apparatus and one or more biological sample container are tracked, wherein tracking comprises maintaining, at the database, an audit trail and log corresponding to activities related to the rack apparatus and one or more biological sample containers.

5. The system of claim 4, further comprising verifying receipt of the rack apparatus and the one or more biological sample containers, wherein the verifying comprises:
checking, via the one or more processors and based at least in part on the identifying of the one or more identifies in the one or more captured images, the rack apparatus and the one or more biological sample containers against a manifest.

6. The system of claim 1, further comprising the operations of:
displaying, via a user interface, a graphical representation of the rack apparatus, the graphical representation including columns and rows; and
displaying, via the user interface, a graphical indication of a status for a particular biological sample container positioned in a respective column/row location.

7. The system of claim 1, further comprising the operations of:
displaying, via a user interface, a graphical representation of a location number of the rack apparatus, the location number representing one of the openings of the rack apparatus, and an associated patient information comprising a patient name or a patient identifier.

8. The system of claim 1, further comprising:
a rack cover attached to the rack apparatus, the rack cover positioned over the plurality of columns and rows of rack openings of the rack apparatus, wherein the rack cover is removeable from the rack apparatus.

9. A computer implemented method for tracking and managing biological samples using a rack apparatus, the method comprising:
receiving, at a first location, the rack apparatus holding one or more biological sample containers, the rack apparatus comprising a plurality of columns and rows of rack openings disposed in a top portion of the rack apparatus, wherein at least one of the plurality of columns comprises a control blank region having two fewer rack openings than the other plurality of columns, and wherein the other plurality of columns of the rack apparatus have an equal number of rack openings and wherein the rack openings are positioned asymmetrically;
removing, a rack cover attached to the rack apparatus, the rack cover positioned over the one or more biological sample containers;
capturing, by a camera module, one or more images of a top portion of one or more biological sample containers positioned in the rack apparatus;
wherein the top surface of a biological sample container includes a graphical identifier representing an identifier with a respective biological sample held within a container;
identifying, via one or more processors, the control blank region in the one or more captured images;
determining, via the one or more processors and based at least in part on the identifying of the control blank region, an orientation of the rack in the one or more captured images;
determining, via the one or more processors and based on the orientation of the rack, a position in the rack apparatus of each biological sample container;
generating, via the one or more processors and based on the determined orientation, a bounding box around each of the one or more biological sample containers in the one or more captured images;
analyzing, via the one or more processors, a region contained within each bounding box in the one or more captured images;
identifying, via the one or more processors and based on analyzing of the region of each bounding box, one or more identifiers in the one or more captured images;
associating, via the one or more processors, each identifier with the determined position;
registering, via the one or more processors, each of the one or more biological sample containers with a sample record, wherein the registration is based on the identified identifier; and
storing in a database, the sample record of each of the one or more biological samples.

10. The method of claim 9, wherein the one or more biological sample containers are filled with biological samples collected from one or more patients at a second location, wherein the second location are and the first location are different.

11. The method of claim 9, wherein the graphical identifier on the top portion of the biological sample container is a QR code or a bar code representing a patient identifier.

12. The method of claim 10, wherein the rack apparatus and one or more biological sample container are tracked, wherein tracking comprises maintaining, at the database, an audit trail and log corresponding to activities related to the rack apparatus and one or more biological sample containers.

13. The method of claim 12, further comprising verifying receipt of the rack apparatus and the one or more biological sample containers, wherein the verifying comprises:
checking, via the one or more processors and based at least in part on the identifying of the one or more identifies in the one or more captured images, the rack apparatus and the one or more biological sample containers against a manifest.

14. The method of claim 9, further comprising the operations of:
displaying, via a user interface, a graphical representation of a rack apparatus, the graphical representation including columns and rows; and
displaying, via the user interface, a graphical indication of a status of a particular biological sample container positioned in a respective column/row location.

15. The method of claim 9, further comprising the operations of:
displaying, via a user interface, a graphical representation of a location number of the rack apparatus, the location number representing one of the openings of the rack apparatus, and an associated patient information comprising a patient name or a patient identifier.

* * * * *